(12) United States Patent  (10) Patent No.: US 12,233,211 B2
Chin et al.  (45) Date of Patent: Feb. 25, 2025

(54) SYSTEMS AND METHODS FOR MITIGATING NOISE AND VIBRATION IN A PORTABLE OXYGEN CONCENTRATOR

(71) Applicant: Inogen, Inc., Goleta, CA (US)

(72) Inventors: Daniel Wayne Chin, Goleta, CA (US); Peter James Hansen, Santa Barbara, CA (US); Brenton Alan Taylor, Kenwood, CA (US)

(73) Assignee: Inogen, Inc., Goleta, CA (US)

( * ) Notice: Subject to any disclaimer, the term of this patent is extended or adjusted under 35 U.S.C. 154(b) by 520 days.

(21) Appl. No.: 17/709,214

(22) Filed: Mar. 30, 2022

(65) Prior Publication Data

US 2022/0313938 A1  Oct. 6, 2022

Related U.S. Application Data

(60) Provisional application No. 63/169,084, filed on Mar. 31, 2021.

(51) Int. Cl.
*B01D 53/22* (2006.01)
*A61M 16/00* (2006.01)
(Continued)

(52) U.S. Cl.
CPC ...... *A61M 16/101* (2014.02); *A61M 16/0063* (2014.02); *B01D 53/0454* (2013.01);
(Continued)

(58) Field of Classification Search
CPC ............ A61M 16/101; A61M 16/0063; A61M 2205/106; A61M 2205/3365;
(Continued)

(56) References Cited

U.S. PATENT DOCUMENTS 5,908,053 A   6/1999  Byrd
6,176,897 B1 * 1/2001  Keefer ............... B01D 53/0476
                                                    96/144
(Continued)

FOREIGN PATENT DOCUMENTS

WO   WO 2007/118054 A2   10/2007

OTHER PUBLICATIONS

Search Report and Written Opinion received in International Application No. PCT/US2022/022610 dated Jul. 11, 2022, in 32 pages.

*Primary Examiner* — Anthony R Shumate
(74) *Attorney, Agent, or Firm* — Knobbe, Martens, Olson & Bear, LLP

(57) ABSTRACT

A portable oxygen concentrator includes a compressor and a controller. The compressor includes a motor, at least one chamber, and at least one piston operably coupled to the motor and movable within the at least one chamber. In some embodiments, the controller is configured to: determine actual motor speeds for commutations steps of the motor during a first rotational cycle; determine an average motor speed during the first rotational cycle; determine a voltage pattern based at least on a comparison of the average motor speed during the first rotational cycle and the actual motor speeds for the commutation steps of the motor during the first rotational cycle; and cause the voltage pattern to be applied to the motor during a second rotational cycle to reduce differences between applied motor torque and variable torque load imparted by the at least one piston.

20 Claims, 14 Drawing Sheets

(51) Int. Cl.
*A61M 16/10* (2006.01)
*B01D 53/04* (2006.01)

(52) U.S. Cl.
CPC .............. *A61M 2205/106* (2013.01); *A61M 2205/3365* (2013.01); *B01D 2253/104* (2013.01); *B01D 2253/108* (2013.01); *B01D 2256/12* (2013.01); *B01D 2257/102* (2013.01); *B01D 2257/504* (2013.01); *B01D 2257/80* (2013.01); *B01D 2259/4533* (2013.01); *B01D 2259/4541* (2013.01)

(58) Field of Classification Search
CPC .......... B01D 53/0454; B01D 2253/104; B01D 2253/108; B01D 2256/12; B01D 2257/102; B01D 2257/504; B01D 2257/80; B01D 2259/4533; B01D 2259/4541
See application file for complete search history.

(56) References Cited

U.S. PATENT DOCUMENTS

| | | | |
|---|---|---|---|
| 6,279,520 B1* | 8/2001 | Lowi, Jr. ................. | F01B 7/02 123/56.1 |
| 6,896,721 B1* | 5/2005 | Lynn ................. | B01D 53/0473 96/116 |
| 7,204,249 B1* | 4/2007 | Richey, II .......... | B01D 53/0446 128/204.22 |
| 7,448,382 B1 | 11/2008 | Alexander et al. | |
| 7,585,351 B2* | 9/2009 | Deane ................... | B01D 53/053 95/138 |
| 7,922,789 B1 | 4/2011 | Deane et al. | |
| 11,083,865 B2* | 8/2021 | Taylor ................. | A61M 16/101 |
| 2004/0050255 A1* | 3/2004 | Simonds ............ | B01D 53/0415 96/109 |
| 2005/0204923 A1 | 9/2005 | Nakamura et al. | |
| 2011/0247622 A1* | 10/2011 | Schneider .......... | A61M 16/107 128/204.23 |
| 2012/0167888 A1* | 7/2012 | Taylor ................... | A61M 16/10 128/205.12 |
| 2015/0098841 A1* | 4/2015 | Corey ..................... | F04B 41/06 417/286 |
| 2017/0281865 A1* | 10/2017 | Wells ................. | A61M 5/14228 |
| 2017/0361052 A1* | 12/2017 | Taylor ................. | A61M 16/0677 |
| 2018/0344963 A1* | 12/2018 | Taylor ................. | B01D 53/047 |
| 2020/0309303 A1* | 10/2020 | Taylor ............... | A61M 16/0875 |

* cited by examiner

SYSTEMS AND METHODS FOR MITIGATING NOISE AND VIBRATION IN A PORTABLE OXYGEN CONCENTRATOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the priority benefit of U.S. Provisional Application No. 63/169,084, filed Mar. 31, 2021 and titled "SYSTEMS AND METHODS FOR MITIGATING NOISE AND VIBRATION IN A PORTABLE OXYGEN CONCENTRATOR", which is hereby incorporated by reference in its entirety.

BACKGROUND

Field

The present disclosure relates to oxygen concentrators for personal use and in particular to portable oxygen concentrators. More particularly, the present disclosure relates to systems and methods for mitigating noise and vibration in portable oxygen concentrators.

Description of the Related Art

Oxygen concentrators are devices that convert ambient air to an oxygen enriched gas for therapeutic use. They are becoming increasingly popular as alternatives to liquid oxygen vessels and compressed gas cylinders. Such personal oxygen concentrators exist in both portable form for ambulatory use and stationary form for use inside the home. To be practical for everyday use by patients needing therapeutic oxygen, portable oxygen concentrators are generally preferred over stationary ones. It is desirable that such portable oxygen concentrators be small, lightweight, efficient, reliable, and relatively inexpensive. It is also desirable for noise and vibration levels in portable oxygen concentrators to be reduced. Efforts to design an oxygen concentrator having all of these desirable attributes may be inherently limited by the size and weight of the individual components.

SUMMARY

To be practical for everyday use by patients needing therapeutic oxygen, it may be advantageous for portable oxygen concentrators to be small in size, light-weight, efficient, reliable, and relatively inexpensive. In particular it may be desirable that portable oxygen concentrators be relatively quiet and free of vibration, especially when carried by user's throughout various environments (for example, inside and outside the user's home). Portable oxygen concentrators traditionally include compressors that receive ambient air, pressurize the received ambient air, and direct the pressurized air toward a gas separation system of the portable oxygen concentrator. Such gas separation system may include one or more adsorbers (for example, adsorbent beds) for separating oxygen from one or more other elements of the air. Such compressors often include a motor, one or more pistons coupled to the motor whose movement is controlled by the motor, and one or more chambers in which the piston(s) move within. In such arrangement, the motor applies a motor torque to the piston(s) during operation and the piston(s) apply a torque load that opposes the motor torque and which varies as the piston(s) move with the chamber(s). Such variable torque load is due at least in part to the changing pressure within the chamber(s) arising from the movement of the piston(s), which is caused by the increasing/decreasing volume defined by the piston(s) within the chamber(s). The variable torque load during piston movement causes large speed oscillations of the motor in the compressor, which in turn causes undesirable noise and vibration of the compressor and the portable oxygen concentrator.

The present disclosure describes portable oxygen concentrators and methods of operating portable oxygen concentrators which minimize speed oscillations of a motor in a compressor, thereby reducing noise and vibration. In various implementations, motor speed oscillations are minimized by controlling operation of the motor in a manner that is responsive to the variable torque load discussed above. As described in more detail below, the motor can be controlled by varying applied voltage over a plurality of commutation steps of the motor during one or more rotational cycles of the motor. In some implementations, a variable voltage pattern is determined based on actual motor speeds during the motor commutation steps during one or more rotational cycles and average motor speeds over such rotational cycle(s), and such voltage pattern is applied (for example, by varying duty cycle) to the motor during one or more subsequent rotational cycles. Such voltage pattern can include a plurality of voltage values that are applied during the plurality of commutations steps, and each of such voltage values can vary with respect to one another and/or with respect to an average voltage over the rotational cycle(s). Multiple voltage patterns can be determined and applied in future rotational cycles of the motor in order to reduce differences between actual motor speeds (at motor commutation steps) and average motor speeds. This in turn reduces differences between the applied motor torque and the torque load, thereby minimizing the noise and vibration of the motor and compressor.

Disclosed herein is a portable oxygen concentrator comprising: a housing; an inlet configured to allow ambient air to flow into an interior of the housing; a gas separation system positioned within the interior; a compressor; and a controller. The compressor can be: positioned within the interior and arranged between the inlet and the gas separation system; and configured to receive and pressurize at least a portion of the ambient air flowing into the interior and direct the portion of the ambient air toward the gas separation system. The gas separation system can include one or more adsorbent beds configured to separate oxygen from one or more other elements in the portion of the ambient air. The compressor can include: a motor; at least one chamber for receiving the portion of the ambient air; and at least one piston coupled to the motor and configured to be moved within the at least one chamber via rotation of the motor. The controller can be configured to: cause a substantially constant average voltage to be applied to the motor during a first rotational cycle of the motor, said motor applying a motor torque to the at least one piston responsive to the application of the substantially constant average voltage, said at least one piston applying a variable torque load to the motor that opposes the motor torque and varies as the at least one piston moves within the at least one chamber; determine, for each of a plurality of commutation steps of the motor during the first rotational cycle, an actual motor speed; determine an average motor speed during the first rotational cycle; determine a plurality of correction terms, each of the plurality of correction terms comprising a difference between the actual motor speed for one of the plurality of commutation steps of the motor during the first rotational cycle and the average motor speed during the first rotational cycle; determine a voltage pattern comprising a plurality of voltage values, each of the plurality of voltage values determined based at least on one of the plurality of correction terms, wherein at least some of the plurality of voltage values differ from the substantially constant average voltage; and cause each of the plurality of voltage values of the voltage pattern to be applied to the motor during a respective one of the plurality of commutation steps for at least a second rotational cycle of the motor, said application of the voltage pattern reducing differences between the applied motor torque and the variable torque load, thereby minimizing speed oscillations of the motor and noise and vibration of the compressor within the portable oxygen concentrator.

In some implementations, the controller is further configured to determine angular position of the motor prior to causing the substantially constant average voltage to be applied to the motor. In some implementations, the controller is configured to determine the angular position of the motor by detecting back EMF. In some implementations, the voltage pattern comprises an oscillating waveform.

In some implementations: each of the plurality of voltage values applied to the motor during the respective one of the plurality of commutation steps for the second rotational cycle is greater than the substantially constant average voltage when an associated one of the actual motor speeds during the respective one of the plurality of commutation steps of the first rotational cycle is less than said average motor speed during the first rotational cycle; and each of the plurality of voltage values applied to the motor during the respective one of the plurality of commutation steps for the second rotational cycle is less than the substantially constant average voltage when the associated one of the actual motor speeds during the respective one of the plurality of commutation steps of the first rotational cycle is greater than said average motor speed during the first rotational cycle. In some implementations: said at least one piston comprises one piston and said at least one chamber comprises one chamber; said variable torque load applied by the piston to the motor comprises a maximum torque load and a minimum torque load; said maximum torque load occurs when the piston is positioned at a location within the chamber such that a volume defined within the chamber is at a minimum value; and said minimum torque load occurs when the piston is positioned at a location within the chamber such that the volume is at a maximum value.

In some implementations, the at least one chamber comprises two chambers and the at least one piston comprises two pistons configured in a reciprocating arrangement. In some implementations, said plurality of commutation steps comprises six commutation steps. In some implementations, the controller is configured to cause said substantially constant average voltage to be applied to the motor via pulse width modulation (PWM). In some implementations, said substantially constant average voltage is associated with one of a plurality of flow settings of the portable oxygen concentrator. In some implementations, said substantially constant average voltage is associated with a desired average RPM of said motor. In some implementations, an average of the plurality of voltage values of the voltage pattern applied to the motor during the second rotational cycle is substantially equal to the substantially constant average voltage applied to the motor during the first rotational cycle.

Disclosed herein is a method of controlling operation of a motor in a compressor to reduce noise and vibration during use. The method can include: determining an actual motor speed for each of a plurality of commutation steps of the motor during a first rotational cycle of the motor; determining an average motor speed during the first rotational cycle, wherein the average motor speed during the first rotational cycle differs from at least one of the actual motor speeds for the plurality of commutation steps during the first rotational cycle; and determining a voltage pattern to be used during at least a second rotational cycle of the motor, said voltage pattern determined based at least on a comparison of said average motor speed and said actual motor speeds for the plurality of commutation steps of the motor during the first rotational cycle.

In some implementations, the method further comprises: determining a charge level of a battery configured to provide power to the motor; and applying said voltage pattern to the motor during the second rotational cycle when said charge level is above a threshold. In some implementations, said voltage pattern comprises an oscillating waveform. In some implementations, said voltage pattern comprises a plurality of voltage values, each of said plurality of voltage values determined based at least on a difference between one of said actual motor speeds for the plurality of commutation steps and said average motor speed during the first rotational cycle.

In some implementations, the method further comprises applying said voltage pattern to the motor during the second rotational cycle of the motor by applying each of said plurality of voltage values to the motor for a respective one of said plurality of commutations steps during said second rotational cycle of the motor. In some implementations: said compressor comprises said motor, at least one chamber, and at least one piston operably coupled to said motor and configured to be moved within the at least one chamber via rotation of the motor; said compressor is positioned within a portable oxygen concentrator; and the method further comprises pressurizing at least a portion of ambient air flowing into an interior of the portable oxygen concentrator and directing said at least the portion of ambient air towards a gas separation system of the portable oxygen concentrator comprising one or more adsorbent beds. In some implementations, said applying said voltage pattern to the motor during the second rotational cycle of the motor occurs prior to or after a pressure swing adsorption cycle of the portable oxygen concentrator. In some implementations, at least one of said plurality of voltage values differs from at least one other one of said plurality of voltage values.

In some implementations, the method further comprises applying a substantially constant average voltage to the motor during the first rotational cycle of the motor, wherein at least one of said plurality of voltage values of said voltage pattern differs from said substantially constant average voltage.

In some implementations: each of the plurality of voltage values associated with a respective one of the plurality of commutation steps during the second rotational cycle is greater than said substantially constant average voltage when an associated one of the actual motor speeds during the respective one of the plurality of commutation steps of the first rotational cycle is less than said average motor speed during the first rotational cycle; and each of the plurality of voltage values associated with the respective one of the plurality of commutation steps during the second rotational cycle is less than said substantially constant average voltage when the associated one of the actual motor speeds during the respective one of the plurality of commutation steps of the first rotational cycle is greater than said average motor speed during the first rotational cycle.

In some implementations, said voltage pattern comprises a first voltage pattern, and the method further comprises: determining an actual motor speed for each of said plurality of commutation steps of the motor during the second rotational cycle of the motor; determining an average motor speed during the second rotational cycle of the motor; and determine a second voltage pattern to be used during at least a third rotational cycle of the motor, said second voltage pattern determined based on a comparison of said average motor speed during the second rotational cycle and the actual motor speeds for the plurality of commutation steps of the motor during the second rotational cycle, wherein said second voltage pattern differs from said first voltage pattern. In some implementations, the first voltage pattern comprises a plurality of voltage values and the second voltage pattern comprises a plurality of voltage values, and wherein at least one of said plurality of voltage values of the second voltage pattern differs from at least one of said plurality of voltage values of the first voltage pattern. In some implementations, the average motor speed during the second rotational cycle of the motor is substantially equal to the average motor speed during the first rotational cycle of the motor. In some implementations, the method further comprises applying said second voltage pattern to the motor during the third rotational cycle of the motor. In some implementations, said first voltage pattern comprises a first waveform and wherein said second voltage pattern comprises a second waveform that is different than the first waveform. In some implementations, the second waveform has a smaller amplitude than the first waveform. In some implementations, each of the first and second waveforms is an oscillating waveform.

Disclosed herein is a portable oxygen concentrator comprising: a compressor and a controller. The compressor can be configured to pressurize and direct ambient air flowing into an interior of the portable oxygen concentrator towards a gas separation system of the portable oxygen concentrator. The compressor can include a motor, at least one chamber for receiving at least a portion of the ambient air, and at least one piston operably coupled to the motor and configured to be moved within the at least one chamber via rotation of the motor, said motor applying a motor torque to the at least one piston responsive to rotation of the motor, said at least one piston applying a variable torque load to the motor that opposes said motor torque and varies as the at least one piston moves within the at least one chamber. The controller can be configured to: determine an actual motor speed for each of a plurality of commutation steps of the motor during a first rotational cycle of the motor; determine an average motor speed during the first rotational cycle, wherein the average motor speed during the first rotational cycle differs from at least one of the actual motor speeds for the plurality of commutation steps during the first rotational cycle; and determine a voltage pattern to be used during a second rotational cycle of the motor, said voltage pattern comprising a plurality of voltage values determined based at least on a comparison of the average motor speed during the first rotational cycle and the actual motor speeds for the plurality of commutation steps of the motor during the first rotational cycle, said voltage pattern usable to reduce differences between said applied motor torque and said variable torque load, thereby minimizing speed oscillations of the motor and noise and vibration of the compressor, wherein at least one of said plurality of voltage values differs from at least one other one of said plurality of voltage values.

In some implementations: the controller is configured to determine each of said plurality of voltage values based at least on one of a plurality of correction terms; and each of the plurality of correction terms comprises a difference between the actual motor speed for one of the plurality of commutation steps of the motor during the first rotational cycle and said average motor speed during said first rotational cycle. In some implementations, the controller is further configured to cause a substantially constant average voltage to be applied to the motor during the first rotational cycle of the motor, said motor applying said motor torque to the at least one piston responsive to said application of the substantially constant average voltage. In some implementations, at least one of said plurality of voltage values differs from said substantially constant average voltage.

In some implementations: each of the plurality of voltage values associated with a respective one of the plurality of commutation steps during the second rotational cycle is greater than said substantially constant average voltage when an associated one of the actual motor speeds during the respective one of the plurality of commutation steps of the first rotational cycle is less than said average motor speed during the first rotational cycle; and each of the plurality of voltage values associated with the respective one of the plurality of commutation steps during the second rotational cycle is less than said substantially constant average voltage when the associated one of the actual motor speeds during the respective one of the plurality of commutation steps of the first rotational cycle is greater than said average motor speed during the first rotational cycle.

In some implementations, the controller is further configured to cause said voltage pattern to be applied to the motor during the second rotational cycle of the motor. In some implementations, the controller is further configured to cause said voltage pattern to be applied to the motor during the second rotational cycle of the motor by causing each of the plurality of voltage values of the voltage pattern to be applied to the motor during a respective one of the plurality of commutation steps during the second rotational cycle of the motor.

In some implementations, the portable oxygen concentrator further comprises a battery, and the controller is further configured to cause said voltage pattern to be applied to the motor during the second rotational cycle of the motor only if a charge level of said battery is above a threshold. In some implementations, the portable oxygen concentrator further comprises a housing and one or more vibration mounts arranged adjacent to the compressor within the housing, said one or more vibration mounts having a harmonic frequency, wherein the controller is further configured to: cause said voltage pattern to be applied to the motor during the second rotational cycle of the motor based on a comparison of said average motor speed during at least said first rotational cycle and said harmonic frequency. In some implementations, the controller is configured to cause said voltage pattern to be applied to the motor during the second rotational cycle of the motor when said average motor speed during at least said first rotational cycle is within a threshold range that includes a motor speed associated with said harmonic frequency. In some implementations, said voltage pattern comprises an oscillating waveform.

In some implementations: said voltage pattern is a first voltage pattern; and the controller is further configured to: determine an actual motor speed for each of said plurality of commutation steps of the motor during the second rotational cycle of the motor; determine an average motor speed during the second rotational cycle of the motor; and determine a second voltage pattern to be used during a third rotational cycle of the motor, said second voltage pattern comprising a plurality of voltage values determined based at least on a comparison of the average motor speed during the second rotational cycle and the actual motor speeds for the plurality of commutation steps of the motor during the second rotational cycle, wherein at least one of said plurality of voltage values of said second voltage pattern differs from at least one other one of said plurality of voltage values of said second voltage pattern.

In some implementations, at least one of said plurality of voltage values of the second voltage pattern differs from at least one of said plurality of voltage values of the first voltage pattern. In some implementations, the average motor speed during the second rotational cycle of the motor is substantially equal to the average motor speed during the first rotational cycle of the motor.

In some implementations, the average motor speed during the second rotational cycle of the motor differs from at least one of the actual motor speeds for the plurality of commutation steps during the second rotational cycle. In some implementations, the first and second voltage patterns comprise a plurality of pairs of voltage values, each of the plurality of pairs of voltage values associated with a respective one of the plurality of commutation steps, and wherein at least one of said plurality of pairs of voltage values comprises different values. In some implementations, the first and second voltage patterns comprise a plurality of pairs of voltage values, each of the plurality of pairs of voltage values associated with a respective one of the plurality of commutation steps, and wherein each of said plurality of pairs of voltage values comprises different values.

In some implementations, the controller is further configured to cause said second voltage pattern to be applied to the motor during the third rotational cycle of the motor. In some implementations, the controller is configured to cause said second voltage pattern to be applied to the motor during the third rotational cycle of the motor by causing each of the plurality of voltage values of the second voltage pattern to be applied to the motor during a respective one of the plurality of commutation steps during the third rotational cycle of the motor. In some implementations, said first voltage pattern comprises a first waveform and wherein said second voltage pattern comprises a second waveform that is different than the first waveform. In some implementations, the second waveform has a smaller amplitude than the first waveform. In some implementations, each of the first and second waveforms is an oscillating waveform.

In some implementations, the controller is further configured to: determine each of said plurality of voltage values of the first voltage pattern based at least on one of a first plurality of correction terms, each of the first plurality of correction terms comprising a difference between the actual motor speed for one of the plurality of commutation steps of the motor during the first rotational cycle and said average motor speed during said first rotational cycle; and determine each of said plurality of voltage values of the second voltage pattern based at least on one of a second plurality of correction terms, each of the second plurality of correction terms comprising a difference between the actual motor speed for one of the plurality of commutation steps of the motor during the second rotational cycle and said average motor speed during said second rotational cycle.

In some implementations, the controller is further configured to: determine a plurality of average actual motor speeds, each of said plurality of average actual motor speeds comprising an average of the actual motor speeds during at least the first and second rotational cycles for one of the plurality of commutation steps; determine an average of said plurality of average actual motor speeds; and determine a third voltage pattern to be used during a fourth rotational cycle of the motor, said third voltage pattern comprising a plurality of voltage values determined based at least on a comparison of: said average of said plurality of average actual motor speeds; and said plurality of average actual motor speeds. In some implementations, said third voltage pattern is different than at least one of said first and second voltage patterns. In some implementations, said third voltage pattern is different than both of said first and second voltage patterns. In some implementations, the controller is further configured to cause said third voltage pattern to be applied to the motor during said fourth rotational cycle of the motor.

Disclosed herein is a method of controlling operation of a motor of a compressor in a portable oxygen concentrator to reduce noise and vibration during use. The compressor can be configured to pressurize and direct ambient air flowing into an interior of the portable oxygen concentrator towards a gas separation system of the portable oxygen concentrator. The compressor can include said motor, at least one chamber for receiving at least a portion of said ambient air, and at least one piston operably coupled to said motor and configured to be moved within the at least one chamber via rotation of said motor, said motor applying a motor torque to the at least one piston responsive to rotation of said motor, said at least one piston applying a variable torque load to the motor that opposes said motor torque and varies as the at least one piston moves within the at least one chamber. The method can include: determining an actual motor speed for each of a plurality of commutation steps of the motor during a first rotational cycle; determining an average motor speed during the first rotational cycle, wherein the average motor speed during the first rotational cycle differs from at least one of the actual motor speeds for the plurality of commutation steps during the first rotational cycle; and determining a voltage pattern to be used during a second rotational cycle of the motor, said voltage pattern comprising a plurality of voltage values determined based at least on a comparison of the average motor speed during the first rotational cycle and the actual motor speeds for the plurality of commutation steps of the motor during the first rotational cycle, said voltage pattern usable to reduce differences between said applied motor torque and said variable torque load, thereby minimizing speed oscillations of the motor and noise and vibration of the compressor, wherein at least one of said plurality of voltage values differs from at least one other one of said plurality of voltage values.

In some implementations, the method further comprises: determining a plurality of correction terms, each of the plurality of correction terms comprising a difference between the actual motor speed for one of the plurality of commutation steps of the motor during the first rotational cycle and said average motor speed during said first rotational cycle, wherein each of said plurality of voltage values is determined based at least on one of said plurality of correction terms. In some implementations, the method further comprises applying a substantially constant average voltage to the motor during the first rotational cycle of the motor, said motor applying said motor torque to the at least one piston responsive to said application of the substantially constant average voltage. In some implementations, at least one of said plurality of voltage values differs from said substantially constant average voltage.

In some implementations: each of the plurality of voltage values associated with a respective one of the plurality of commutation steps during the second rotational cycle is greater than said substantially constant average voltage when an associated one of the actual motor speeds during the respective one of the plurality of commutation steps of the first rotational cycle is less than said average motor speed during the first rotational cycle; and each of the plurality of voltage values associated with the respective one of the plurality of commutation steps during the second rotational cycle is less than said substantially constant average voltage when the associated one of the actual motor speeds during the respective one of the plurality of commutation steps of the first rotational cycle is greater than said average motor speed during the first rotational cycle.

In some implementations, the method further comprises applying said voltage pattern to the motor during the second rotational cycle of the motor. In some implementations, said applying said voltage pattern to the motor during the second rotational cycle of the motor comprises applying each of the plurality of voltage values of the voltage pattern to the motor during a respective one of the plurality of commutation steps during the second rotational cycle of the motor. In some implementations, the method further comprises: determining a charge level of a battery of the portable oxygen concentrator; and applying said voltage pattern to the motor during the second rotational cycle when said charge level is above a threshold.

In some implementations, the portable oxygen concentrator further comprises a housing and one or more vibration mounts arranged adjacent to the compressor within the housing, said one or more vibration mounts having a harmonic frequency, and the method further comprises: applying said voltage pattern to the motor during the second rotational cycle of the motor based on a comparison of said average motor speed during at least said first rotational cycle and said harmonic frequency.

In some implementations, the method further comprises applying said voltage pattern to the motor during the second rotational cycle of the motor when said average motor speed during at least said first rotational cycle is within a threshold range that includes a motor speed associated with said harmonic frequency. In some implementations, said voltage pattern is a first voltage pattern and the method further comprises: determining an actual motor speed for each of said plurality of commutation steps of the motor during the second rotational cycle of the motor; determining an average motor speed during the second rotational cycle of the motor; and determining a second voltage pattern to be used during a third rotational cycle of the motor, said second voltage pattern comprising a plurality of voltage values determined based at least on a comparison of the average motor speed during the second rotational cycle and the actual motor speeds for the plurality of commutation steps of the motor during the second rotational cycle, wherein at least one of said plurality of voltage values of said second voltage pattern differs from at least one other one of said plurality of voltage values of said second voltage pattern.

In some implementations, at least one of said plurality of voltage values of the second voltage pattern differs from at least one of said plurality of voltage values of the first voltage pattern. In some implementations, the average motor speed during the second rotational cycle of the motor is substantially equal to the average motor speed during the first rotational cycle of the motor. In some implementations, the average motor speed during the second rotational cycle of the motor differs from at least one of the actual motor speeds for the plurality of commutation steps during the second rotational cycle. In some implementations, the first and second voltage patterns comprise a plurality of pairs of voltage values, each of the plurality of pairs of voltage values associated with a respective one of the plurality of commutation steps, and wherein at least one of said plurality of pairs of voltage values comprises different values. In some implementations, the first and second voltage patterns comprise a plurality of pairs of voltage values, each of the plurality of pairs of voltage values associated with a respective one of the plurality of commutation steps, and wherein each of said plurality of pairs of voltage values comprises different values.

In some implementations, said first voltage pattern comprises a first waveform and wherein said second voltage pattern comprises a second waveform that is different than the first waveform. In some implementations, the second waveform has a smaller amplitude than the first waveform. In some implementations, each of the first and second waveforms is an oscillating waveform.

In some implementations, the method further comprises: determining a first plurality of correction terms, each of the first plurality of correction terms comprising a difference between the actual motor speed for one of the plurality of commutation steps of the motor during the first rotational cycle and said average motor speed during said first rotational cycle, wherein each of said plurality of voltage values of the first voltage pattern is determined based at least on one of said plurality of correction terms; and determining a second plurality of correction terms, each of the second plurality of correction terms comprising a difference between the actual motor speed for one of the plurality of commutation steps of the motor during the second rotational cycle and said average motor speed during said second rotational cycle, wherein each of said plurality of voltage values of the second voltage pattern is determined based at least on one of said second plurality of correction terms.

In some implementations, the method further comprises: determining a plurality of average actual motor speeds, each of said plurality of average actual motor speeds comprising an average of the actual motor speeds during at least the first and second rotational cycles for one of the plurality of commutation steps; determining an average of said plurality of average actual motor speeds; and determining a third voltage pattern to be used during a fourth rotational cycle of the motor, said third voltage pattern comprising a plurality of voltage values determined based on a comparison of: said average of said plurality of average actual motor speeds; and said plurality of average actual motor speeds.

In some implementations, said third voltage pattern is different than at least one of said first and second voltage patterns. In some implementations, said third voltage pattern is different than both of said first and second voltage patterns. In some implementations, the method further comprises applying said third voltage pattern to the motor during said fourth rotational cycle of the motor.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIG. 7A illustrates an example compressor and compressor mounts while

DETAILED DESCRIPTION

Personal use therapeutic oxygen concentrators that convert ambient air into oxygen enriched gas are increasing in popularity, both in portable and stationary forms. They are generally much smaller in size and different in design as compared to industrial gas concentrators. Examples of small, portable, personal use concentrators are described in U.S. Pat. No. 10,695,520, titled "Gas Concentrator with Removable Cartridge Adsorbent Beds", U.S. Pat. No. 10,786,644, titled "Gas Concentrator with Removable Cartridge Adsorbent Beds", U.S. Pat. No. 11,083,865, titled "Compact Portable Oxygen Concentrator", and U.S. patent application Ser. No. 16/837,816, titled "Compact Portable Oxygen Concentrator", all of which are incorporated by reference herein in their entireties. Such concentrators, because of their small size and intended personal use, have differing design considerations from large industrial concentrators intended to produce large quantities of concentrated gases. Some implementations of the portable oxygen concentrators disclosed herein are between approximately 100 and 200 cubic inches in size, between 2 and 7 pounds in weight (for example, less than 7 pounds), and/or may produce between approximately 300 and 2000 ml/min of concentrated oxygen (for example, between approximately 600 and 1300 ml/min of concentrated oxygen).

Figure 1:
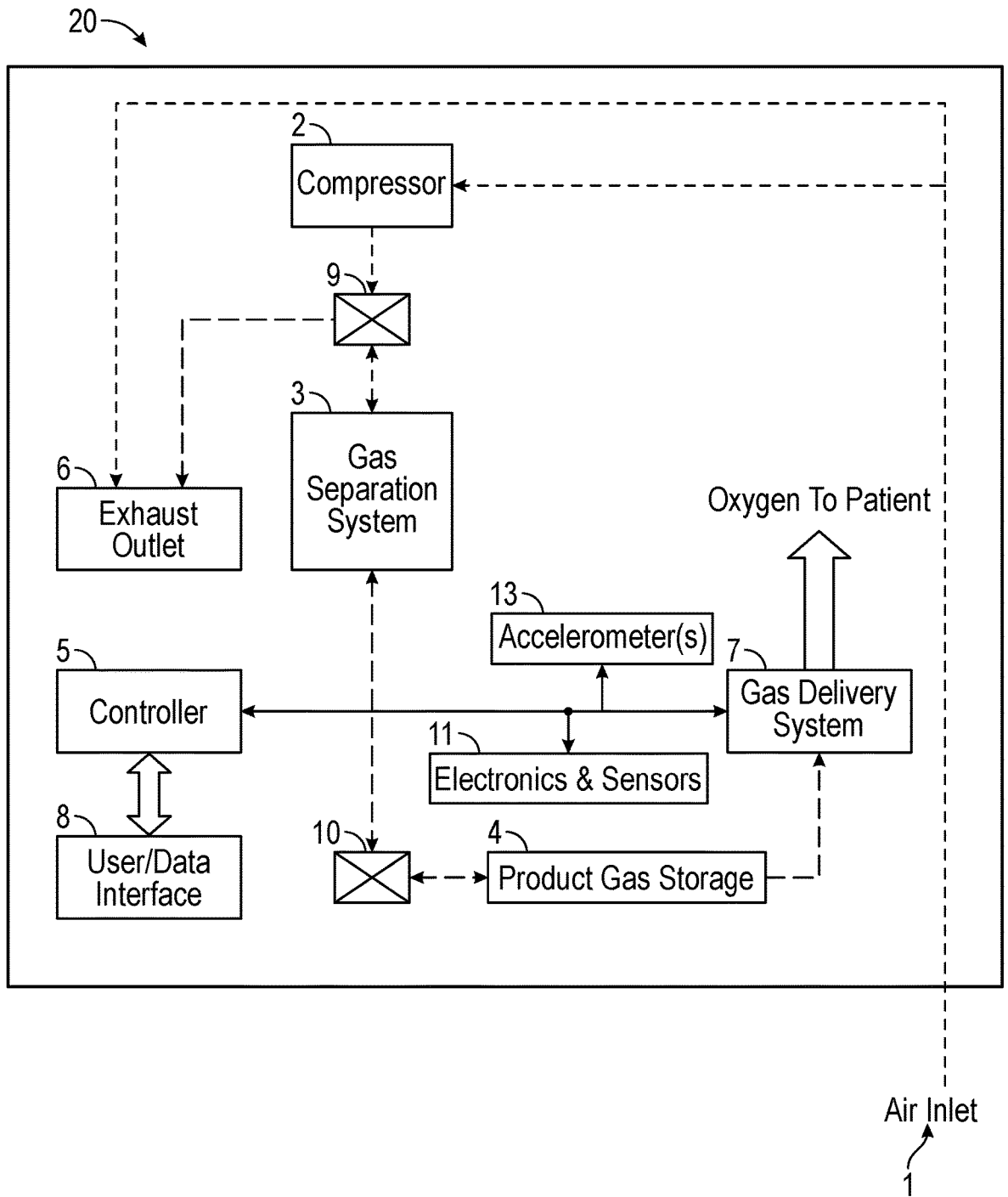
FIG. 1 shows a simplified schematic diagram of an example oxygen concentrator in accordance with aspects of this disclosure.

FIG. 1 is a schematic illustration of an example oxygen concentrator system 20 in accordance with the present disclosure. System 20 can be incorporated in one or more components of a portable oxygen concentrator (such as a housing), for example. As shown, the system 20 generally includes an air inlet 1 through which ambient air is drawn into the system 20, a compressor 2 for pressurizing at least a portion of the ambient air to provide a feed gas, a gas separation system 3 (which may also be referred to as a "gas separation section") which receives and processes the feed gas to produce a product gas having a higher oxygen content than the portion of the ambient air, a gas delivery system 7 (such as a conserver) for delivering oxygen-rich product gas to a patient, and an exhaust outlet 6 for releasing nitrogen-rich waste gas and/or spent cooling airflow gas. As used herein, spent cooling airflow gas can refer to airflow gas that has been used to cool portions of the system 20. System 20 can further include a feed/waste manifold 9, a product valve manifold 10, a product gas storage 4, a user/data interface 8, and a controller 5 (for example, a programmable controller) for controlling the operation of the system 20 or portions thereof (for example, a motor within the compressor 2 as discussed in more detail below). Controller 5 can be configured to control operation of a motor of the compressor 2 in accordance with any of the methods discussed in this disclosure.

In some embodiments, ambient air drawn into the system 20 through air inlet 1 can be used to supply the gas separation system 3 with pressurized gas to move (for example, "flush") out the nitrogen-rich waste gas. Ambient air drawn into the system 20 through the air inlet 1 can also be used to cool the internal components of the system. This air movement may be provided by an airflow generator (such as a fan or blower) located at the air inlet 1, at the exhaust outlet 6, or along an air flow path between the air inlet 1 and the exhaust outlet 6 (for example, centrally in such air flow path). To achieve proper air flow, an airflow generator may be employed in some embodiments. In some embodiments, airflow may be generated, for example, by a cooling fan or blower. In some embodiments, the cooling fan or blower has dimensions in the range of 40 mm×40 mm to 100 mm×100 mm in diameter and 20 mm to 60 mm in depth. One or more or a plurality of fans in varying sizes and locations may also be employed in some embodiments to optimize air flow and/or minimize noise. As indicated schematically in FIG. 1, air flow may be directed to pass over internal components of the oxygen concentrator system 20. In some embodiments, the waste gas from the gas separation system 3 and the spent cooling gas both exit the system 20 via the exhaust outlet 6. In some embodiments, the exhaust outlet 6 is positioned adjacent or immediately adjacent the compressor 2. In some embodiments, the air flow path directs cool air to pass over the other components of the system 20 before reaching the compressor 2. In some cases, the compressor 2 may generate significant heat during operation. For example, the compressor 2 may be the largest source of heat in the system 20. In some embodiments, the compressor 2 is placed adjacent to the exhaust outlet 6 to achieve improved cooling effectiveness. In some embodiments, an airflow generator (such as a fan, blower, or other means) may be positioned along the air flow path to push and/or pull air through the system 20 interior from the air inlet 1 to the exhaust outlet 6 or between the air inlet 1 and the exhaust outlet 6. In some embodiments, a plurality of air inlets and/or a plurality of exhaust outlets may be employed to achieve appropriate cooling. In some embodiments, the system 20 can include a plurality of airflow generators to achieve appropriate cooling.

In some embodiments, the gas separation system 3 is a pressure swing adsorption (PSA) gas separation system. In some embodiments, the gas separation system 3 is a vacuum swing adsorption (VSA) system. In some embodiments, the gas separation system 3 is a vacuum pressure swing adsorption (VPSA) system. The gas separation system 3 may include one or more adsorbers. The adsorbers can employ pressure, vacuum, or a combination thereof to separate the components of ambient air to produce an oxygen-rich product gas. In some embodiments, ambient air is drawn in by the compressor 2 through a filter and through an elongated and/or tortuous air path designed to minimize the escape of noise caused by the compressor 2. In some embodiments, the compressor 2 may be a single cylinder or multi-cylinder reciprocating piston compressor employing pressure or a combination of pressure and vacuum cylinders. In some variants, the compressor 2 may alternatively or additionally be of another compressor type, such as scroll, linear free piston, rotary vane, rotary screw, conical screw, or diaphragm type compressors.

Pressurized air may be discharged from the compressor 2 at a rate of approximately 5 SLPM to 15 SLPM per LPM, for example at a pressure up to 3 bar, although other rates and/or pressures are possible. The pressurized air can be directed to one of two or more adsorbers of the gas separation system 3 by one or more feed/waste valves that may be housed in a feed/waste manifold 9. The feed/waste valve configuration can vary by embodiment and may include one or more solenoid valves, piezoelectric valves, air piloted valves, rotary valves, cam actuated valves, and/or diaphragm valves. In some embodiments, the feed/waste valves may be decoupled from the compressor 2, adsorber(s) of the gas separation system 3, and/or other structural components to minimize transmission of noise from the valves to other system components or the exterior of the system 20. A valve fluid path may be connected with compliant members to achieve an appropriate level of mechanical isolation and the feed/waste manifold 9 or valve mounting can be additionally isolated from other components. Alternatively, in some embodiments, the valves may be directly mounted to relatively high-mass, high density components, such as a compressor head of the compressor 2 or the adsorbers of the gas separation system 3 to minimize noise transmission. These components may also then be isolated from other components in the system 20, particularly large plastic bodies such as housings and/or chassis components. The feed/waste valves contained in feed/waste manifold 9 can additionally direct nitrogen-rich exhaust gas from the adsorbers of the gas separation system 3 to a muffler in a pressure swing adsorption (PSA) system or to a vacuum pump in a vacuum swing adsorption (VSA) or vacuum pressure swing adsorption (VPSA) system.

In some embodiments, the adsorbers of the gas separation system 3 are designed to be removable and replaceable as described in one or more of the above incorporated references. Each adsorber can include an adsorbent material and a vessel housing the adsorbent material. The adsorbent material can be in the form of an adsorbent bed. The adsorbent bed(s) may contain at least one pretreatment adsorbent layer that is directed to water and carbon dioxide removal to prevent contamination of a main layer adsorbent. In some embodiments, this material may be a desiccant such as activated alumina or silica gel. In alternate embodiments, the pretreatment layer may contain a sodium or lithium exchanged zeolite. The adsorbent bed(s) can also include a main layer adsorbent that is directed to separate oxygen from nitrogen in ambient air. The main layer adsorbent may be a lithium exchanged zeolite material. Nitrogen is retained in the adsorber, while oxygen-rich gas is allowed to pass through the adsorber into the product valves or product valve manifold 10.

The product valve manifold 10 may include one or more of solenoid valves, piezoelectric valves, air piloted valves, rotary valves, cam actuated valves, or diaphragm valves, check valves, and orifices to control gas flow. The product valve manifold 10 can be connected to the adsorber(s) of the gas separation system 3 and may be decoupled from the adsorber(s) and other structural components to minimize noise transmission and vibration between valves and other components in the system 20. The product valve manifold 10 may also be part of a common assembly with the feed/waste valve manifold 9 with appropriate portions of the valve directing gas into and out of the adsorber(s) of the gas separation system 3.

In some embodiments, oxygen-rich gas flows from the product valve manifold 10 to an integrated assembly that is directed to product gas storage 4, oxygen gas concentration measurement, oxygen gas pressure and/or temperature sensing, oxygen gas filtration, and/or oxygen gas delivery (for example, a gas delivery system 7). In some embodiments, the gas delivery system 7 is a conserver. In some embodiments, the integrated assembly contains one or more sensors 11 for various functions including ambient pressure sensing, oxygen gas pressure measurement, breath pressure and/or cannula pressure measurement, and/or temperature measurement.

The control of the gas concentrator can be achieved by a controller 5. The controller 5 can be in communication with a motor of the compressor 2 and can cause the motor to operate (for example, by causing voltage to be applied to the motor). The controller 5 can include one or more processors. In some implementations, such one or more processors are in communication with a memory. In some implementations, the controller 5 is embodied in a printed circuit board (PCB). The system 20 also may contain a user/data interface 8. The user/data interface 8 can include one or more buttons or inputs to control various aspects or functions of the system 20, such as, for example, power state, oxygen flow rate, flow setting, and/or any other aspect or function of system 20. Other embodiments additionally contain an LCD display, at least one removable and rechargeable battery, and/or an integrated oxygen conserving device to deliver oxygen gas synchronously with a patient's onset of inhalation to maintain clinical efficacy while reducing the amount of oxygen gas delivered to the patient by a factor of about 2:1 to 9:1, for example. The controller 5 can be in communication with the user/data interface 8 and can be responsive to the user/data interface 8. For example, the controller 6 can receive instructions based on input into the user/data interface 8 and can control operation of the system 20 (for example, control operation of the motor of the compressor 2) based on said input. Such input may involve changing a flow rate and/or flow setting of the system 20, which may be achieved by changing characteristics of the motor of the compressor 2 (for example, increase an average RPM of the motor of the compressor 2). As another example, in some implementations, the user/data interface 8 can be utilized to cause the system 20 (for example, controller 5) to enable or disable utilization of any of the motor control methods discussed elsewhere herein (for example, method 300).

In some embodiments, system 20 includes one or more accelerometers 13. Accelerometer(s) 13 may be used to determine orientation and/or movement, but may also be used, as described elsewhere herein, to measure vibration of the compressor 2 and/or other portions of system 20 (and/or a portable oxygen concentrator which incorporates system 20). Accelerometer(s) 13 can be in communication with controller 5 to enable controller 5 to receive and/or process one or more signals outputted by the accelerometer(s) 13. In some embodiments, controller 5 alters characteristics of a motor of the compressor 2 responsive to one or more signals received from the accelerometer(s) 13 and/or responsive to a comparison of such signal(s) to a threshold. Such embodiments may allow the controller 5 to stop or change a speed of the motor of the compressor 2 responsive to such comparison, for example. As an example, in some implementations, the accelerometer(s) 13 can be utilized to cause the system 20 (for example, controller 5) to enable or disable utilization of any of the motor control methods discussed elsewhere herein (for example, method 300) when detected acceleration signal(s) are above a threshold value that may be indicative of a level of movement of the system 20 (which may be incorporated in a portable oxygen concentrator). As another example, in some implementations, controller 5 is configured to enable utilization of any of the motor control methods discussed elsewhere herein (for example, method 300) when detected vibration is above a threshold value and/or disable utilization of any of such motor control methods when detected vibration is below such threshold value.

In some embodiments, system 20 includes a battery, which may be rechargeable. In some embodiments, controller 5 alters characteristics of a motor of the compressor 2 responsive to a charge level of the battery. For example, in some implementations, the controller 5 is configured to stop or change a speed of the motor of the compressor 2 responsive to determining that the charge level of the battery is below a threshold value. As another example, in some implementations, the controller 5 is configured to cause the system 20 to enable utilization of any of the motor control methods discussed elsewhere herein (for example, method 300) when the charge level is above such threshold value and/or disable utilization of any of such motor control methods when the charge level is below such threshold value.

The compressor 2 can include a motor, one or more pistons coupled to the motor and configured to be moved by the motor (for example, via rotation of the motor), and one or more chambers (for example, cylinders) configured to receive a portion of ambient air drawn into the compressor 2. In some implementations, the compressor 2 includes two pistons and two chambers. In some implementations, the compressor 2 includes an alternative number of pistons, such as three, four, five, or six or more pistons. In some implementations, the compressor 2 includes one piston and one chamber. The motor of the compressor 2 can (for example, via rotation) drive the piston(s) and cause the piston(s) to move within respective chambers. Operation of the motor can be controlled using the controller 5. The motor can be operated using various methods, for example, depending on the motor type and/or configuration. The motor of the compressor can be an AC or DC motor. The motor can be, for example, a brushless DC (BLDC) motor. One or more signals indicative of information of the motor of the compressor 2 can be outputted by the motor and/or a sensor coupled with the motor. Such signal(s) can be indicative of information such as position of a rotor of the motor, rotation time (for example, time at and/or between one or more of a plurality of commutation steps of the motor), speed, and/or other data indicative of, or related to, the angular velocity of the motor (for example, of the rotor of the motor). Such information can be utilized to control operation of the motor, such as applied voltage, as explained in more detail below. Various sensing means can be utilized to obtain information about the motor (for example, speed, position, etc.), such as Hall effect sensors, optical sensors (such as encoders), back electromotive force (EMF) in a drive circuit, and/or other sensing means. In some variants, system 20 includes an additional controller (separate from controller 5) that may be in communication with controller 5 and may be configured to cause operation of the motor of the compressor 2. Controller 5 can be configured to cause the motor of the compressor 2 to rotate, for example, via application of voltage such as described in more detail elsewhere herein. Various techniques can be utilized for applying voltage to the motor of the compressor 2. Controller 5 can be configured to vary applied voltage for one or more commutation step of the motor, for example, by varying duty cycle.

Figure 2A:
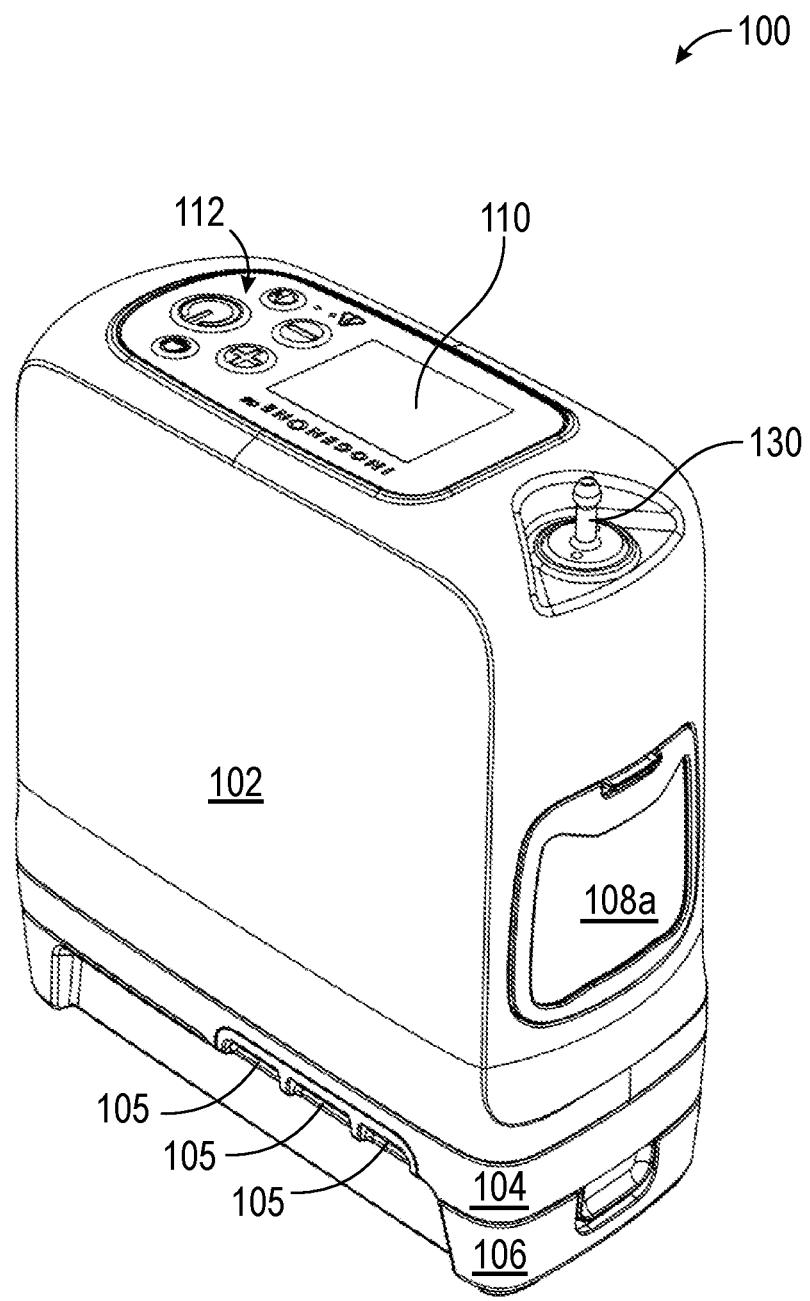
FIGS. 2A-2B illustrate an example portable oxygen concentrator and portions thereof in accordance with aspects of this disclosure.
Figure 2B:
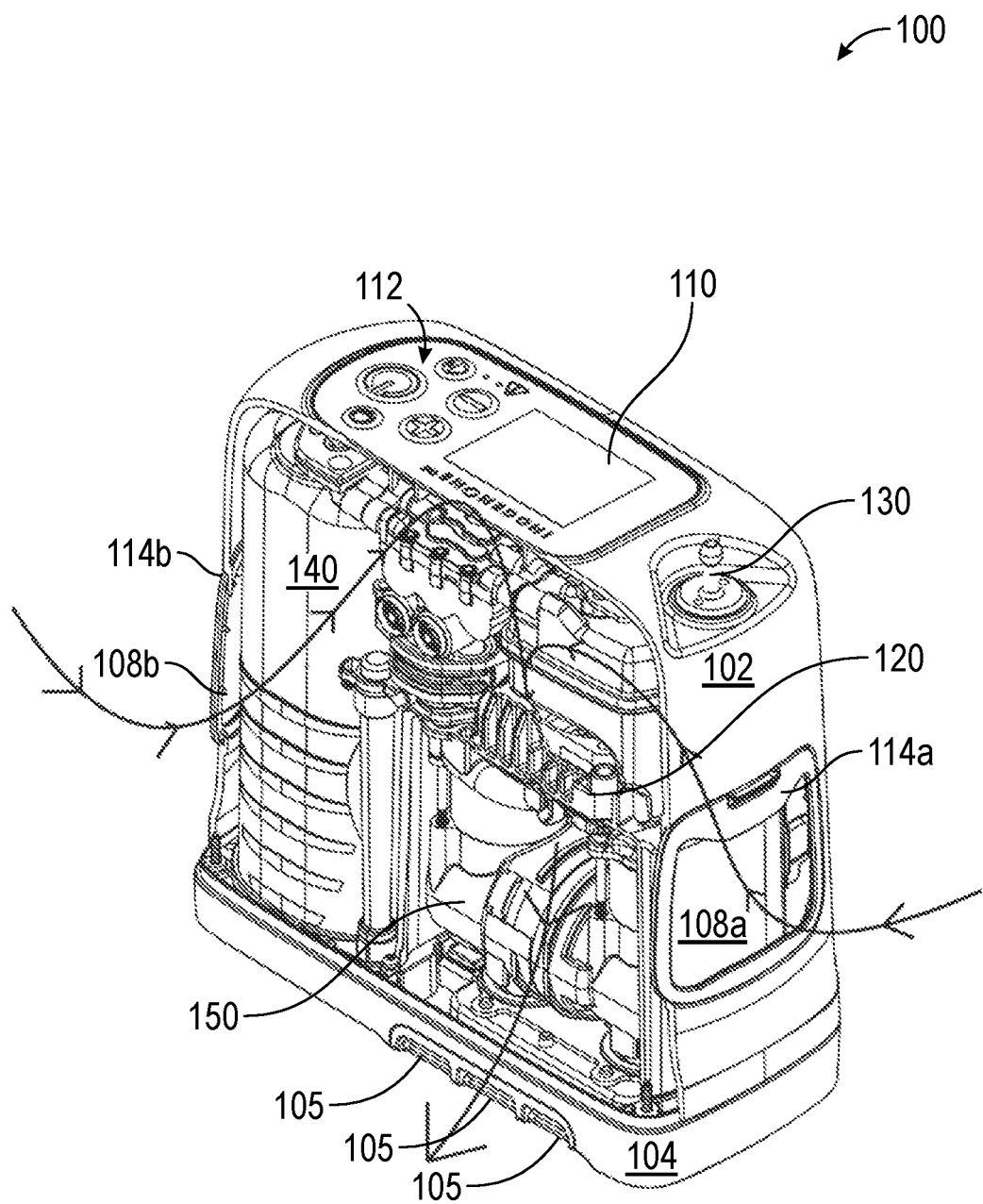

FIGS. 2A-2B illustrate a portable oxygen concentrator 100, which may be an embodiment of the oxygen concentrator system 20. The oxygen concentrator 100 can include any of the same or similar features and/or functions as the system 20. The oxygen concentrator 100 can include any of the same or similar features and/or functions as described with respect to any of the oxygen concentrators described in U.S. patent application Ser. No. 16/837,816, titled "COMPACT PORTABLE OXYGEN CONCENTRATOR", which is incorporated by reference herein in its entirety.

FIG. 2A illustrates a perspective view of the oxygen concentrator 100 and FIG. 2B illustrates a perspective view of the oxygen concentrator 100 with a portion of a housing 102 thereof removed. The oxygen concentrator 100 can include a housing 102 (which may be referred to as an "outer housing") that can enclose one or more components of the oxygen concentrator 100. In some embodiments, the oxygen concentrator 100 includes a chassis base 104. The housing 102 and chassis base 104 can be removably connectable to one another in some implementations. The housing 102 can define an interior alone and/or in combination with chassis base 104. The chassis base 104 (which may also be referred to as a "dual function chassis base") can serve as a support for the internal components of the oxygen concentrator 100. The chassis base 104 can also serve as a mount for a power source, such as a battery. In some implementations, oxygen concentrator 100 includes a battery 106 that can removably connect to the chassis base 104. With reference to FIG. 2B, an interior of the oxygen concentrator 100 (for example, formed by housing 102 and/or chassis base 104) can house one or more adsorbers 140, an airflow generator 120, a compressor 150, each of which are described further below and are shown in one or more of FIGS. 2B-2C.

The oxygen concentrator 100 can further include one or more user interface controls, a user interface display 110, and/or one or more printed circuit boards (PCBs). Oxygen concentrator 100 can include a gas delivery output, such as output port 130 shown in FIG. 2A which can output oxygen-rich air, for example, to a tube connected thereto. The one or more PCBs of the oxygen concentrator 100 can be a user interface display/sensor PCB or sensor block PCB, or include both. The one or more PCBs can include and/or be coupled with various control sensors such as oxygen purity, pressure, and temperature sensors. In some embodiments, the oxygen concentrator 100 includes shell structure (such as one or more insulating panels) enclosing at least a portion of a compressor 150, similar or identical to that described in U.S. patent application Ser. No. 16/837,816. As shown in FIG. 2B, the portable oxygen concentrator 100 can include one or more adsorbers 140. In some embodiments, the adsorber(s) 140 are non-cylindrical adsorbers. The vessels forming the adsorber(s) 140 can be generally non-cylindrical in shape. The adsorber(s) 140 can be similar or identical to the adsorber(s) discussed with reference to gas separation system 3 of oxygen concentrator system 20 described above. The oxygen concentrator 100 can a controller that can be similar or identical to any of the controllers discussed herein and that can be configured to carry out any of the motor control methods described herein.

With reference to FIG. 2B, the oxygen concentrator 100 can include an airflow generator 120. The airflow generator 120 can be mounted directly over the compressor 150 in some implementations. The airflow generator 120 can be a blower or fan. The outer housing 102 can include one or more air inlets 108*a-b*. The air inlets 108*a-b* can be recessed within the outer housing 102 or extend along a curved or angled surface of the outer housing 102. In some embodiments, the air inlet 108*a* and the air inlet 108*b* can be positioned on different faces or surfaces of the outer housing 102. In some embodiments, the air inlet 108*a* and the air inlet 108*b* can be positioned on opposite surfaces of the outer housing 102. Air can be drawn in from two sides of the oxygen concentrator 100 through the air inlets 108*a* and 108*b* disposed on opposing sides of the oxygen concentrator 100. Curved arrowed lines in FIG. 2B illustrate example air flow into, within, and out of the oxygen concentrator 100. In alternative embodiments, the air inlet 108*a* and the air inlet 108*b* can be positioned on the same face or surface of the outer housing 102. In some embodiments, internal components can be positioned such that cooler outside air flows over most of the internal components before being directed to the vicinity of the compressor 150.

The airflow generator 120 is configured to direct airflow along an airflow path between the one or more air inlets 108*a-b* and one or more exhaust outlets 105. In some embodiments, one or more exhaust outlets 105 can be positioned within the chassis base 104. In some embodiments, the chassis base 104 can include exhaust port(s) 105 on opposite side surfaces of the chassis base 104 (for example, on the side surface of chassis base 104 that is seen in FIG. 2B and on an opposite side surface). Both exhaust gas from the PSA gas separation system (which can include adsorber(s) 140) and the fully downstream spent cooling gas can be exhausted through exhaust ports 105 on each side of chassis base 104. In alternative embodiments, the exhaust ports 105 can be positioned on the same side of the chassis base 104. In some embodiments, higher temperature, spent cooling airflow is confined to the area surrounding the compressor 150 and exhausted immediately adjacent the bottom of the compressor 150. This is an example of a push/pull airflow in which the compressor 150 is positioned at a downstream end of the airflow path immediately before the exhaust ports 105. Such an arrangement can accomplish the delivery of cool air to many of or most of the internal components before exhausting hot air from the higher temperature components in the vicinity of the compressor 150. In some embodiments, it is desirable to exhaust hot air in the vicinity of the compressor as soon as possible, for example, to reduce backflow of the higher temperature air from the vicinity of the compressor 150 to other internal regions of the concentrator 100. The positioning of the exhaust ports 105 adjacent to the compressor 150 can reduce such a backflow. Advantageously, the cooling air flow path of the oxygen concentrator system 100 ends at an area adjacent the component that generates the most heat, for example, the compressor 150, so that the spent cooling air can be expelled before affecting other components.

The oxygen concentrator 100 is configured to minimize the likelihood of impeding the airflow through the device in as many use situations as possible such as, for example, placing the oxygen concentrator 100 against a flat vertical surface or laying the concentrator 100 on its side (other than the intended bottom side). The air inlets 108*a* and 108*b* can be designed and arranged to substantially reduce the risk of inlet vent obstruction. In some embodiments, the exhaust ports 105 are contoured such that they cannot be blocked by any single plane. In one embodiment, the exhaust ports 105 are disposed on only one side of the chassis base 104 such that the ports 105 directs hot exhaust gas away from the patient's body when the oxygen concentrator 100 is being carried adjacent to the patient body such as in a shoulder bag or hip bag. In some embodiments, the design of the air inlets 108*a-b* and/or exhaust ports 105 can include additional geometrical details such as curvature of a face of the air inlets 108*a-b* and/or exhaust ports 105, recessing of the air inlets 108*a-b* and/or exhaust ports 105 below the surface of the concentrator housing 102, and/or angling of the exhaust ports 105 to direct both air flow and noise in a desirable direction as it exits the concentrator system 100. In some embodiments, the exhaust ports 105 are angled away from removable battery 106 coupled to the chassis base 104 to prevent heating of the battery 106. In some embodiments, the exhaust ports 105 can be formed in a portion of the chassis base 104 extending laterally beyond a lateral edge of the battery 106. In some embodiments, the exhaust ports 105 are directed at a downward angle over a recess formed in the portion of the chassis base 104 extending laterally beyond a lateral edge of the battery 106. The angling and positioning of the exhaust ports 105 can prevent obstruction of the exhausts ports 105 if the concentrator is placed against or adjacent a flat surface.

In some embodiments, each air inlet 108*a-b* includes an opening defined by an exterior border 114*a-b* that is recessed from a portion of the exterior surface of the housing 102, which may have a planar or convex contour. In some embodiments, the recessed exterior borders 114*a-b* of the air inlets 108*a-b* in combination with the convex contour of the exterior surface of the housing 102 form an air gap that permits at least some air to flow through even when the exterior surface of the housing is resting against a planar surface such as a table top. In some embodiments, a middle section of each exterior border 114*a-b* is not coplanar with the opposing end sections such that the middle section slightly protrudes from the opposing end sections. In some embodiments, the air inlets 108*a-b* comprise louvers having a curved configuration adapted to increase intake of airflow from multiple directions.

Figure 2C:
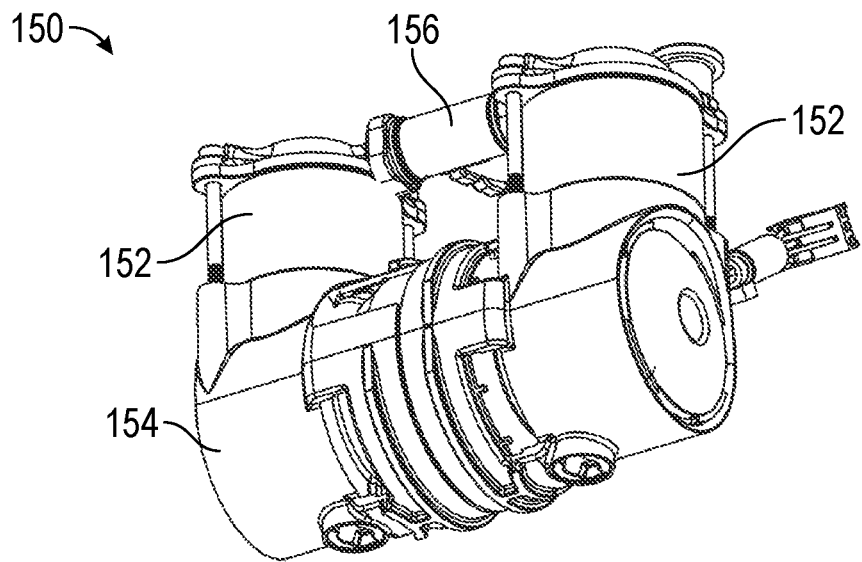
FIG. 2C illustrates a configuration for a compressor of the portable oxygen concentrator of FIGS. 2A-2B in accordance with aspects of this disclosure.

FIG. 2C illustrates the compressor 150 of the oxygen concentrator 100. The compressor 150 can include chambers 152 in which pistons can be arranged and a body 154 that can house a motor of the compressor 150. The compressor 150 can be connected to a tube 156. Compressor 150 and tube 156 can be similar or identical to the compressor and tube described in U.S. patent application Ser. No. 16/837,816, in some implementations.

Figure 2D:
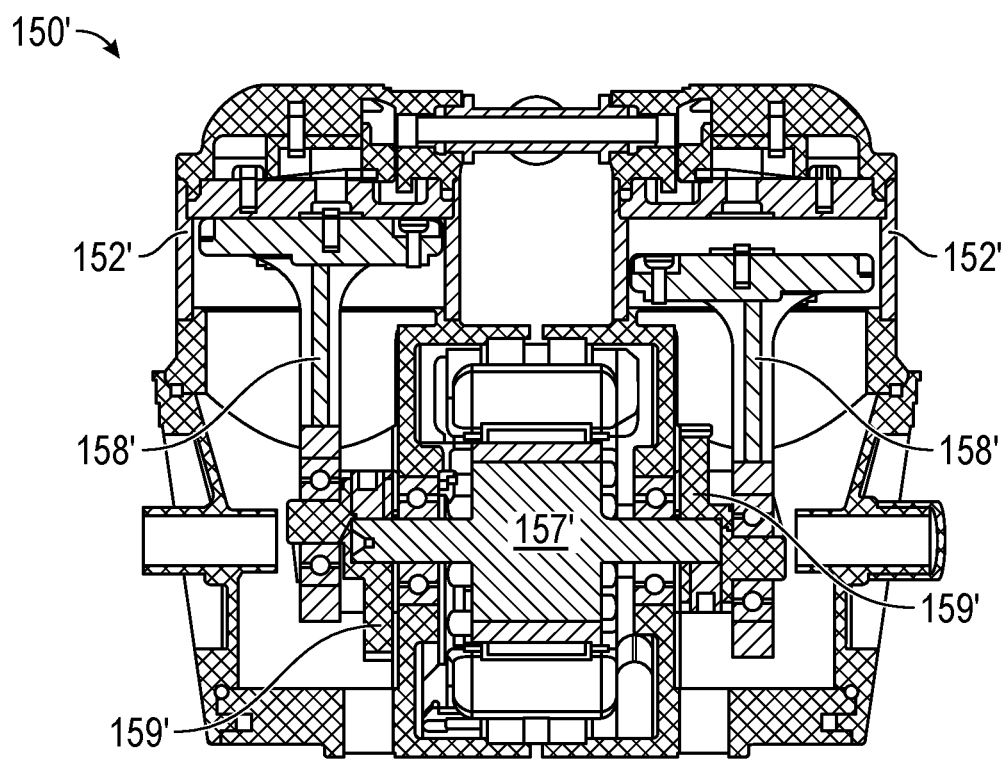
FIG. 2D illustrates an example cross-sectional view of a compressor in accordance with aspects of this disclosure.

FIG. 2D illustrates an example cross-sectional view of a compressor 150' that can be utilized in any of the oxygen concentrators and/or systems described herein (such as oxygen concentrator system 20 and/or oxygen concentrator 100). The compressor 150' can include any of the same or similar features or functions as any of the compressors described herein (for example, compressor 2 or compressor 150). FIG. 2D illustrates chambers 152', pistons 158' arranged within chambers 152', and a motor 157' of the compressor 150'. FIG. 2D also illustrates eccentric counterweights 159' that can be coupled at or near the connection of the motor 157' and the pistons 158'. Motor 157' is coupled to pistons 158' and can cause movement of pistons 158' within chambers 152', for example, when the motor 157' is energized. Motor 157' can be controlled by a controller of an oxygen concentrator which compressor 150' is part of, and such controller can be similar to or identical to any of the controllers discussed herein (such as controller 5). Such controller can cause the motor 157' to rotate (for example, cause a rotor of the motor 157' to rotate) which in turn causes the pistons 158' to move up and down within chambers 152' from and/or between top dead center positions and bottom dead center positions, as illustrated in FIG. 2D (where the piston 158' on the left is shown in a top dead center position and the piston 158' on the right is shown in a bottom dead center position). Motor 157' can rotate (and in turn cause movement of pistons 112') when voltage is applied to motor 157'. Motor 157' generally imparts a motor torque to the pistons 158' when rotated. The pistons 158' impart a torque load responsive to application of motor torque by the motor 157', and such torque load opposes the motor torque. Such torque load varies depending on where the piston(s) 158' are within the chamber(s) 152' over the piston movement cycle as described in more detail below.

Motor 157' can be controlled in accordance with a variety of techniques to step through a plurality of commutations steps (which may also be referred to herein as "commutation sectors") over a rotational cycle of the motor 157'. In some implementations, motor 157' is configured to step through 6, 12, or another number of commutations steps during each rotational cycle. Average speed of the motor 157' can be controlled by increasing or decreasing the average voltage or pulse width modulation (PWM) frequency, or both. Angular position of the motor 157' can be determined by a variety of means. In some implementations, angular position of the motor 157' is determined using back EMF. In alternative implementations, angular position of the motor 157' is determined using another means, such as a Hall effect sensor. Motor 157' can be of a variety of types, such as any of those discussed herein. In some implementations, motor 157' is a DC motor, such as a BLDC motor.

Figure 2E:
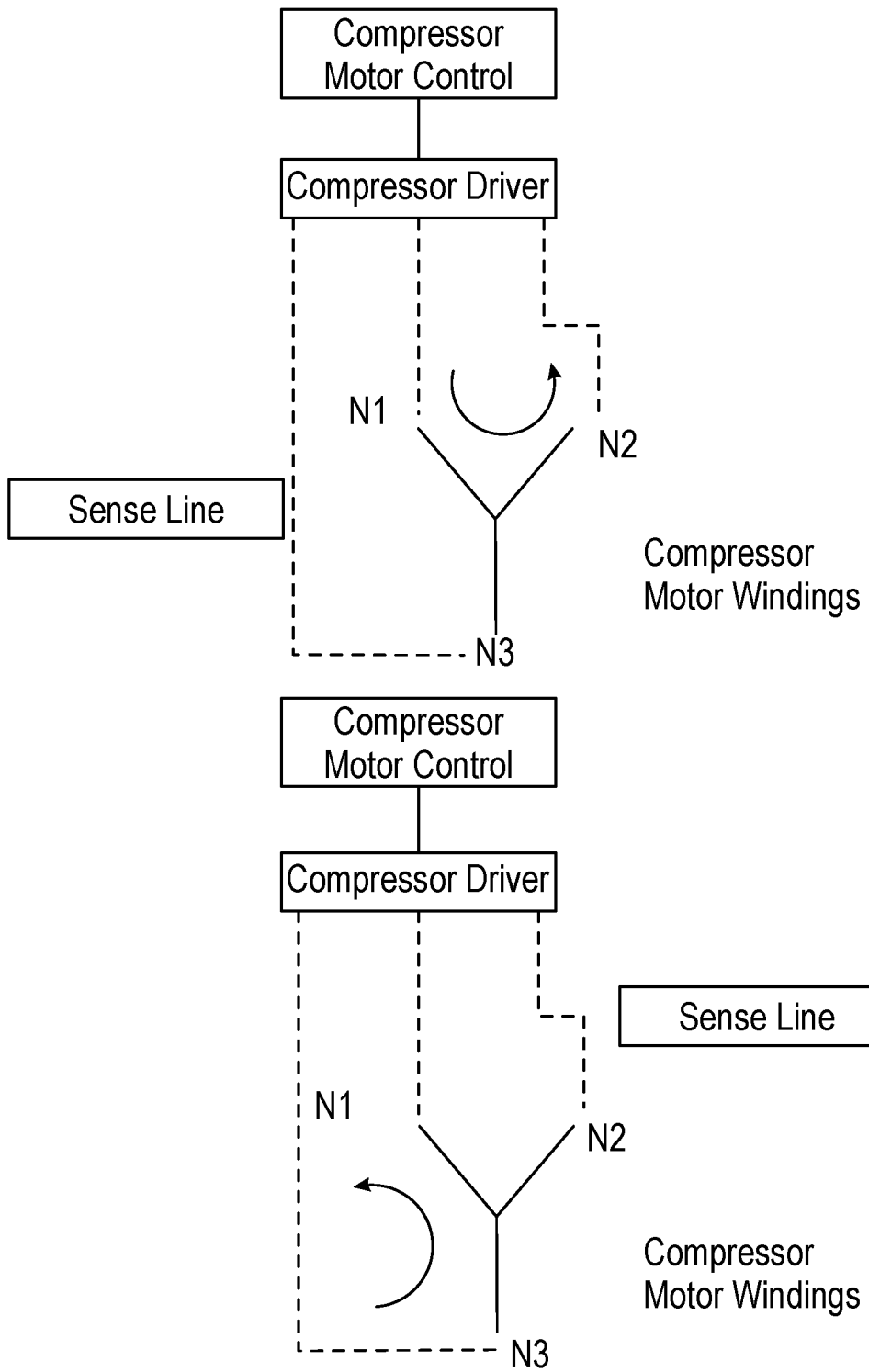
FIG. 2E illustrates a simplified schematic diagram of a configuration for a motor in accordance with aspects of this disclosure.

FIG. 2E illustrates a simplified schematic diagram of an implementation of motor 157'. In such implementation, the motor stator magnetic field can be cycled through 6 states during each 360° electrical revolution. In the illustrated implementation of FIG. 2E, motor 157' is a 3-phase motor and is driven by a "wye" configuration drive. Three phases with one high, one low results in six possible states corresponding to six magnetic vector states, of which two successive states corresponding to two commutation steps are shown. During each rotational cycle the stator magnetic field can be stepped through these 6 steps. Maximum efficiency and torque can be provided where the stator magnetic vector is as close to 90° as possible from the rotor magnetic vector. This may require detection of rotor position to determine which of the 6 stator states should be used. Hall sensors are commonly used to detect the magnetic poles of the rotor permanent magnet, but "sensorless" motor control can be achieved using back EMF detection. In a "wye" configuration, two stator legs (see "N1" and "N2" are driven, the third leg (see "N3") is floating. At sufficient rotational velocity, the permanent magnet of the rotor induces a back EMF. The voltage measured at the third leg can be used by a controller (such as any of the controllers discussed herein) to estimate rotor position.

It is generally advantageous for portable oxygen concentrators to be small and lightweight to be practical for daily use. Therefore, the utilization of a small and lightweight compressor (including a motor) that can operate at a wide range of motor speeds that can provide a variety of flow rates can be advantageous. Multi-step (for example, 6-step) motor control for portable oxygen concentrators provides a relatively simple and effective means with generally low computational requirements.

Reciprocating piston technology, such as that used in many portable oxygen concentrator compressors and as illustrated in FIG. 2D, may have performance issues due to inertial effects and/or varying levels of pressure in the chambers. With reference to compressor 150' including pistons 158', torque load increases as the pistons 158' travel from a bottom dead center position to a top dead center position, as a function of increasing pressure (due to decreasing volume) in accordance with Boyle's law of $P_1V_1=P_2V_2$. As the pistons 158' move from the top dead center position to the bottom dead center position, the torque load decreases, and can generate a positive torque as well from the residual pressure pushing the pistons 158' down. An average torque load value is defined over an entire 360 degree mechanical cycle, and in some scenarios can be much lower than a peak torque load value. Given a fixed motor voltage (and/or PWM duty cycle), an increased torque load results in a negative angular acceleration of the motor. A decreased torque load results in a positive angular acceleration of the motor. Given a fixed motor voltage, the torque loading and unloading results in a motor angular velocity variation that matches (for example, is proportional to) the torque load variation. The amount of torque load variation in a particular compressor of an oxygen concentrator may vary depending on characteristics of the compressor (for example, size of chambers 152' and/or pistons 158', with reference to compressor 150'). Regardless of the precise type of arrangement of the compressor, however, torque load variations may cause significant speed oscillations of the motor if inertia in the system is not sufficient to moderate such variations. Significant speed oscillations can in turn greatly increase noise and vibration of the compressor, and can also increase the likelihood of a stall condition of the motor of the compressor in some situations.

Some compressors (such as compressor 150') utilize two pistons. Such configurations can reduce the effects of torque load variation compared to compressors with only one piston, alternately pressurizing one piston during the first 0-180 degrees of the cycle, and pressurizing the second piston during 180 to 360 degrees of the cycle. This may lower torque load peaks by half, as compared to a comparable output single piston compressor, and may spread the torque loads more evenly across the cycle, which can result in the average torque load (over a single piston cycle) being closer to a given actual instantaneous torque load (at a given location of the piston during its movement cycle). However, in two piston compressors, inherent mechanical inertia in the compressor may be insufficient at lower speeds and can result in significant speed swings at lower speed settings (e.g., RPM) of the compressor, causing high vibration and stall conditions.

While the problem of significantly varying torque loads over a torque load cycle is not strictly limited to portable oxygen concentrator applications, the options to mitigate the issues are not always compatible with the difficult design trade-offs desired in portable oxygen concentrator design, namely, to minimize size, weight, and noise/vibration produced, while maintaining adequate output capacity at the lowest possible cost. For example, a traditional solution of adding extra rotating mass (e.g., flywheels) can be effective, but at higher part costs and part weights. Eccentric counterweights (such as eccentric counterweights 159' shown in FIG. 2D), which can convert motor shaft rotation into properly sequenced piston movement, are relatively large compared to overall compressor dimensions in portable oxygen concentrators, and if made out of heavy materials could serve as ready-made flywheels to provide mechanical inertia. However, increasing the weight of such eccentric counterweights is not a desirable approach for portable oxygen concentrators that are preferably as light as possible to be practical for daily (and often continuous) use. While weight can be minimized with lightweight hubs and mass in a ring at larger diameters, space/size can then become a problem given the desire to have portable oxygen concentrator with small dimensions. Although sophisticated torque management motor control schemes (such as Field Optimized (motor) Control (FOC)) to control operation of a motor of a compressor are an option to address torque load variation, such schemes require significant amounts of processing power, powerful processors, and furthermore may limit the choice of appropriate motor types. As such, existing torque load management techniques, both mechanical solutions and sophisticated, processor-intensive motor control algorithms, are not particularly suitable for use in controlling operation of motors in compressors of portable oxygen concentrators.

In order to mitigate negative effects of the intra-cycle torque load variation (e.g., motor speed oscillations and, in turn, noise/vibration), motor control methods such as those described herein can be utilized. Implementations of motor control methods described herein control operation of the motor of the compressor in a manner that reduces differences between the applied motor torque and the variable torque load during rotation of the motor, which in turn can minimize motor speed oscillations. Any of the methods described herein may be referred to as a "motor control scheme" or a "torque load compensation scheme". Some implementations of the methods described herein reduce the differences between applied motor torque and variable torque load by adjusting motor input (for example, applied voltage) during rotational cycle(s) of the motor in order to reduce differences between actual motor speeds and average motor speed during such rotational cycle(s). Such motor input adjustment can involve varying voltage (for example, by applying a voltage pattern) across the commutation steps of the motor over a rotational cycle based on differences between actual motor speed at each commutation step of the rotational cycle and the average motor speed over the rotational cycle. Because actual motor speed variation can match (for example, be proportional to) variable torque load, reducing differences between actual motor speeds and average motor speeds over rotational cycle(s) can in turn reduce difference between applied motor torque and variable torque load.

In some cases of a portable oxygen concentrator compressor driven by a BLDC motor, the change in torque load can vary by 50% or more within a 60° commutation step of the motor. In some embodiments, this can represent a floor for a minimum error of a technique for controlling operation of a motor based on the variable torque load. Since it may not be desirable to use added inertia weight or sophisticated, processing and/or power intensive control schemes, a suitable torque load compensation scheme for portable oxygen concentrators to match motor torque provided to a generally instantaneous torque load is desirable. It is also desirable that such a scheme should be compatible with standard multi-step motor commutation control schemes that can be implemented at reasonable computation complexities using cost/weight/power appropriate motor choices in portable oxygen concentrators.

Figure 3:
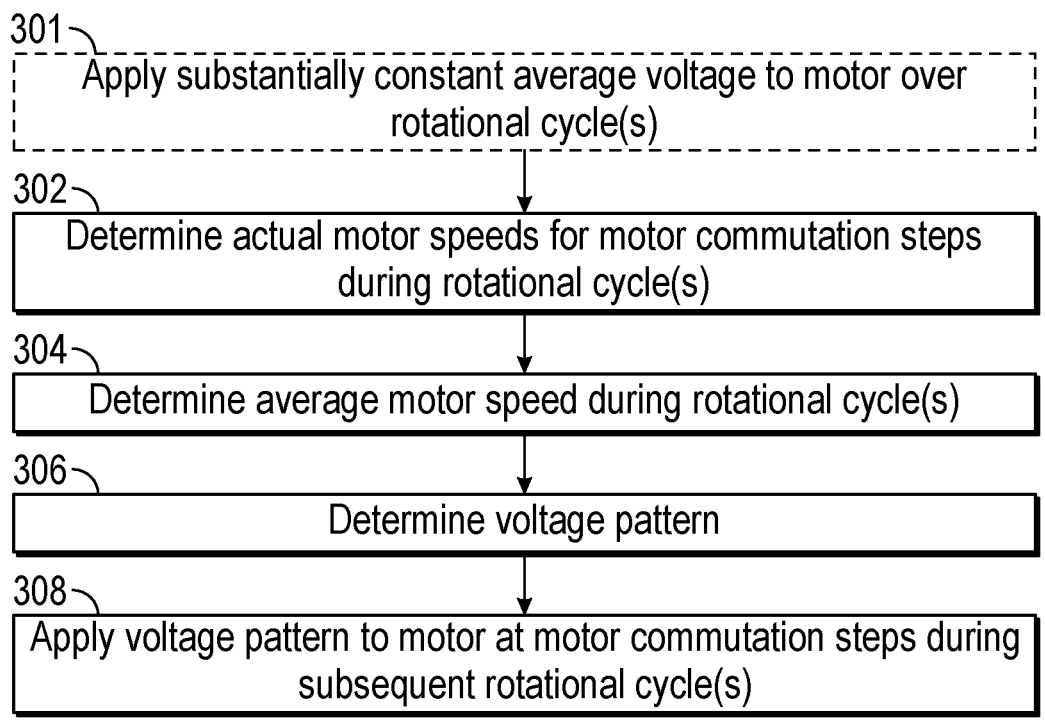
FIG. 3 illustrates a method of controlling operation of a motor in accordance with aspects of this disclosure.

FIG. 3 illustrates a method 300 for controlling operation of a motor of a compressor to reduce differences between motor torque and torque load, thereby minimizing motor speed oscillations and noise and vibration of the compressor. Method 300 can be utilized by any of the oxygen concentrators/systems described herein, such as oxygen concentrator system 20 and/or oxygen concentrator 100. Any of the steps described below can be performed by one or more controllers of any of the oxygen concentrators/systems described herein, such as controller 5.

Any of the motors described herein (including those discussed below with respect to method 300) can utilize stepwise motor commutation, whereby, commutation of the motor through each rotational cycle occurs via a plurality of commutations steps, such as 6, 12, or another number of commutations steps as is well understood by one of skill in the art. Stepwise motor commutation can be a suitable technique for portable oxygen concentrators use as well as for other applications. Such commutation can be controlled by a controller of a portable oxygen concentrator, such as any of those discussed herein. In carrying out operation of the motor and any of the aspects described herein, angular position of the rotor of the motor can be determined at various stages during motor commutation. Angular position can be determined (for example, by the controller) in a variety of ways. For example, the motor can include and/or be in communication with sensors that output one or more signals indicative of angular position of the motor rotor, such as magnetic position sensors, Hall effect sensors, optical sensors. In some implementations, back EMF can be utilized to determine angular position, such as described elsewhere herein. Information obtained in relation to angular position can also be utilized to determine speed of the motor for each of a plurality of commutation steps of the motor during one or more rotational cycles, for example. In some implementations, rotor position is determined for each of a plurality of steps. For example, rotor position can be determined every 60° of electrical revolution. Actual motor speed can be determined based on the timing of a given rotation amount (for example, by timing a 60° of rotation).

Conventional techniques for operating a motor in a compressor of an oxygen concentrator involve applying a substantially constant average voltage to the motor over one or more rotational cycles of the motor (for example, by applying a constant duty cycle). To achieve different average motor speeds, the substantially constant average voltage is either increased or reduced. Such motor control may be referred to as "DC control", and may be achieved with the use of a conventional PD or PID controller where average motor speed is used as a feedback input (which may be referred to as a "feedback control scheme"). However, such motor control results in large speed oscillations of the motor due to significant torque load variation over piston and motor rotational cycles, which in turn causes significant noise and vibration.

Advantageously, method 300 can be utilized to "match" (e.g., bring closer together) the motor torque to the variable torque load in a portable oxygen concentrator compressor to mitigate such issues. Reducing noise and vibration is important for portable devices intended to be worn and/or carried by users, especially when utilized on a regular basis during daily activities. A secondary benefit of matching the applied motor torque to the variable torque load is a decrease in the stall RPM of the compressor. In some cases, for example, where the motor is operating at low speeds, the motor may stall if the torque load is sufficiently high to bring the actual motor speed to zero. Without matching the torque load (for example, through voltage control as described herein), the stall RPM is typically determined by the peak torque load in a given piston movement cycle. By varying motor torque (for example, through voltage control of the motor) to match the torque load using the techniques described herein, lower motor speeds can be utilized without stalling the motor, which in turn may allow lower flow settings in a portable oxygen concentrator than in an oxygen concentrator that does not vary motor torque to match the torque load using the techniques described herein. This is significantly beneficial for portable oxygen concentrators to allow a wider overall range of flow settings. Another benefit of matching the applied motor torque to the variable torque load is that it does not require the addition of larger weight rotational masses (e.g., heavier eccentric counterweights), thereby allowing the portable oxygen concentrator to be as lightweight as possible.

With reference to FIG. 3, method 300 can include: (1) determining actual motor speed for each of a plurality of commutation steps of the motor during a rotational cycle of the motor (step 302); (2) determining an average motor speed over the rotational cycle (step 304); (3) determining a voltage pattern based at least in part on the actual motor speeds for each of the plurality of commutation steps of the motor during the rotational cycle and the average motor speed over the rotational cycle (step 306); and (4) applying the voltage pattern during one or more subsequent rotational cycles of the motor (step 308). Each of steps 302-308 are described in more detail below. Method 300 can include additional or alternative steps, however. Further, in some cases, method 300 involves one or more, but not all of, steps 302-308. For example, in some variations, method 300 includes steps 302, 304, and 306, but not step 308 (for example, if a charge level of a battery that provides power to the motor is below a threshold value such that it may not be desirable to carry out step 308 so that battery life can be preserved). Method 300 can be utilized to match applied motor torque to variable torque load by determining differences between actual motor speeds at different points/regions in a rotational cycle and average motor speeds over the rotational cycle and varying input voltage to the motor during the rotational cycle, in view of the fact that actual motor speed variation is indicative of such torque load variation.

Step 302 generally involves determining actual motor speed for one or more of a plurality of commutation steps of the motor during a given rotational cycle. As mentioned previously, such plurality of commutation steps can be 6, 12, or some other number. Actual motor speed can be determined based on the amount of time required for the motor to rotate between a fixed angle, for example, 60° where 6 steps occur over a 360° rotational cycle. In some implementations, actual motor speed is determined for each of the plurality of commutations steps of a rotational cycle. In some implementations, actual motor speed is not determined for each of the plurality of commutations steps of a rotational cycle, but rather, for some amount less than that (for example, at every other one of the plurality of commutation step).

At step 304, average motor speed is determined over a rotational cycle. Average motor speed can be determined by taking an average of the actual motor speeds for the plurality of commutation steps over the rotational cycle.

At step 306, a voltage pattern can be determined. Step 306 generally requires that steps 302 and 304 have been carried out for at least one rotational cycle of the motor. Such voltage pattern can include a plurality of voltage values and can be utilized during one or more subsequent rotational cycles. Such voltage pattern can be determined based at least in part on a comparison of the actual motor speeds for the plurality of commutation steps over at least one rotational cycle and the average motor speed over the rotational cycle. For example, such voltage pattern can be determined based at least in part on differences between the actual motor speeds for the plurality of commutation steps over the rotational cycle and the average motor speed over the rotational cycle. Method 300 can include determining a plurality of correction terms, each of the correction terms comprising a difference between the actual motor speed for one of the plurality of commutation steps of the motor during the rotational cycle and the average motor speed during the rotational cycle. The voltage pattern determined at step 306 can include a plurality of voltage values and each of the plurality of voltage values can be associated with one of the plurality of commutation steps of the motor. Each of the plurality of voltage values can be determined based at least on one of the plurality of correction terms discussed above. Accordingly, each of the plurality of voltage values of the voltage pattern can be determined based at least on a difference between the actual motor speed for one of the plurality of commutation steps during the rotational cycle and the average motor speed over the rotational cycle.

In some implementations, voltage values for respective commutation steps of the motor can be determined based on whether respective actual motor speeds are higher or lower than average motor speeds. For example, if an actual motor speed for a given commutation step during a first rotational cycle is less than the average motor speed during the first rotational cycle, one of the plurality of voltage values intended to be applied to the motor for that commutation step during a second, subsequent rotational cycle can be greater than a previous value for that commutation step. As another example, if an actual motor speed for a given commutation step during a first rotational cycle is greater than the average motor speed during the first rotational cycle, one of the plurality of voltage values intended to be applied to the motor for that commutation step during the second, subsequent rotational cycle can be smaller than a previous value for that commutation step. In some implementations, the voltage value associated with the respective commutation step during the second rotational cycle is greater or less than the voltage value associated with the respective commutation step during the first rotational cycle by an amount that is proportional to the difference between the actual motor speed for the respective commutation step during the first rotational cycle and the average motor speed during the first rotational cycle. In some implementations, the voltage value associated with the respective commutation step during the first rotational cycle is scaled by a scale factor to obtain the voltage value intended to be applied to the motor for that commutation step during the second rotational cycle, and such scale factor can be based at least on the difference between the actual motor speed for the respective commutation step during the first rotational cycle and the average motor speed during the first rotational cycle.

The plurality of voltage values in the voltage pattern can vary from one another. For example, at least one of the plurality of voltage values can be different from at least one other one of the plurality of voltage values. In some cases, the voltage pattern can be a waveform, for example, an oscillating waveform, defined by the plurality of voltage values. In some implementations, the voltage pattern determined based on motor speed information from a first rotational cycle of the motor (and to be utilized during a second, subsequent rotational cycle), for example, as described above, can be similar to a pattern of the torque load on the motor during the first rotational cycle (for example, can have a similar shape). For example, the shape of the voltage pattern can vary in a similar manner as a shape of torque load variation.

In some implementations of step 306, an input array is generated that includes a plurality of values associated with time for each commutation step (for example, motor speed values). An output array (which may be referred to as a "control array") can be generated and can include a plurality of values, each of which is associated with a value of the input array. The values of the control array can be updated (for example, in sign and/or value) and be voltage values to be applied in future rotational cycles of the motor.

After a voltage pattern is determined at step 306, such voltage pattern can be applied to the motor during one or more subsequent rotational cycles of the motor at step 308. Such voltage pattern can be applied by applying each of the plurality of voltage values of the voltage pattern (determined based on motor speed information obtained from the previous rotational cycle or multiple previous rotational cycles) during a respective one of the plurality commutations steps of the subsequent cycle. As an example, each of the plurality of voltage values determined based at least on a difference between an actual motor speed for a commutation step and the average motor speed during a first rotational cycle can be applied at the respective commutation step during a second rotational cycle. Application of the voltage pattern can be achieved with a controller in communication with the motor, for example, by varying duty cycle.

Figure 4A:
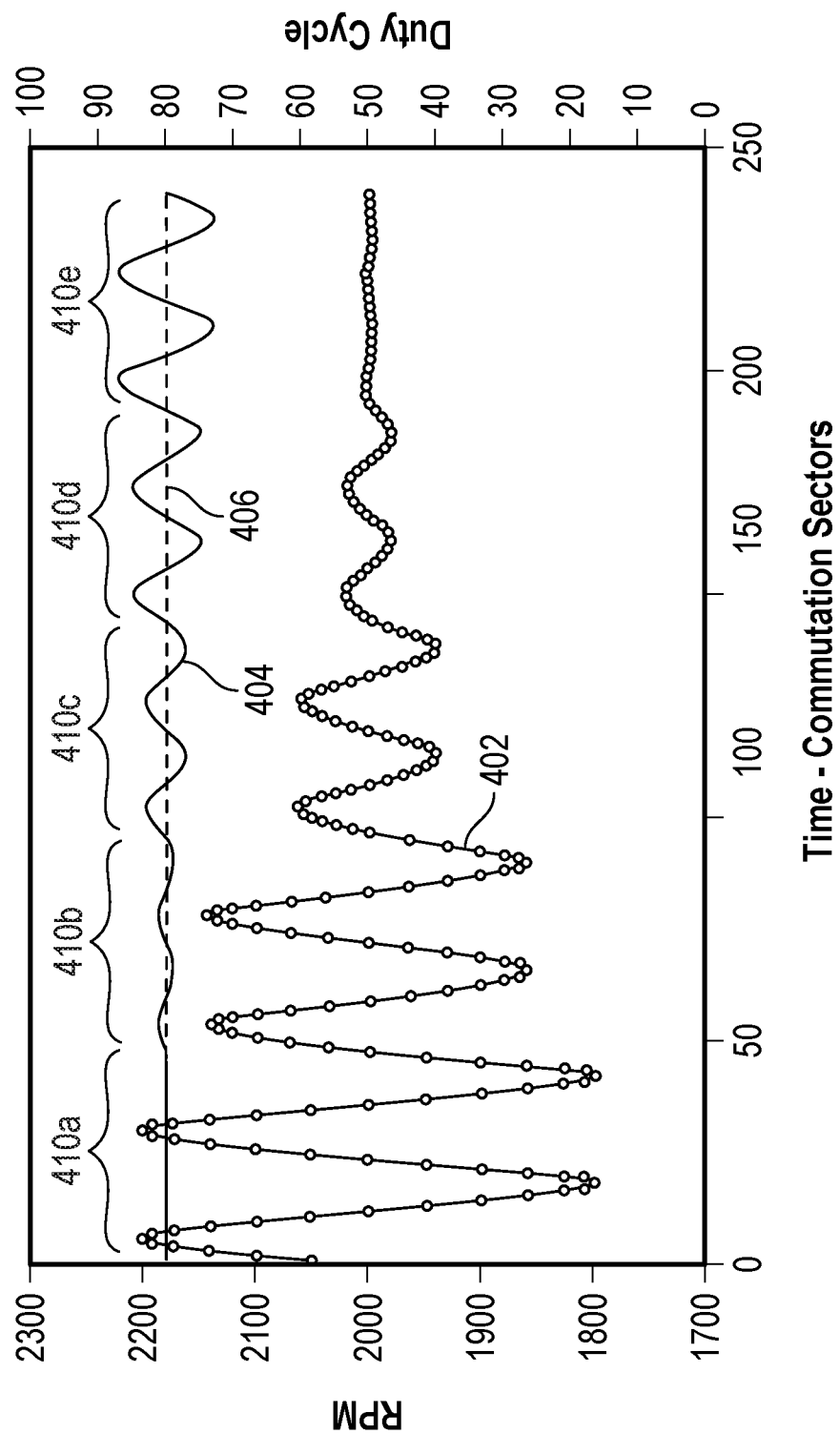
FIGS. 4A-4E graphically illustrate methods of controlling operation of a motor in accordance with aspects of this disclosure.

Steps 302-308 can be repeated over time for a number of rotational cycles of the motor, and voltage patterns can continuously or intermittently be determined and applied as described above in order to modify applied voltage to the motor with the goal of reducing the differences between average motor speed over rotational cycle(s) and actual motor speeds at the motor commutations steps. This in turn has the effect of dynamically "matching" applied motor torque to torque load, thereby minimizing speed oscillations and reducing noise and vibration of the motor as discussed elsewhere herein. In some implementations, as method 300 is carried out for a number of rotational cycles of the motor, successive voltage patterns can vary from one another (for example, in shape and/or amplitude). For example, a first voltage pattern applied during a second rotational cycle of the motor can be different from a second voltage pattern (determined based on information obtained from a first rotational cycle) applied during a third rotational cycle of the motor, and so on. In some implementations, the first and second voltage patterns have a waveform shape (for example, comprising a plurality of voltage values). In some implementations, as the motor control method is continually carried out, successive waveforms (defined by voltage patterns) have increasing amplitude, for example, as shown in FIG. 4A and as further discussed below. For example, a second voltage pattern determined can have a waveform that has maximum and/or minimum points that are greater than (e.g., in absolute value) respective maximum and/or minimum points (e.g., associated with particular motor commutation steps) of a first voltage pattern determined based on previous a rotational cycle that the rotational cycle from which the second voltage pattern is determined.

In some circumstances, a substantially constant average voltage may be applied to the motor for at least one rotational cycle of the motor. This may occur when the motor is turned "on", for example, or at or during another point during motor operation. Such substantially constant average voltage may be applied across all of a plurality of commutation steps of the motor during each of the at least one rotational cycle(s), in contrast to the voltage pattern described above which varies across motor commutation steps. Step 301 in FIG. 3 illustrates such substantially constant average voltage, which may occur prior to step 302, and/or at any point thereafter (for example, if the motor is turned "off" and then "on"). Such substantially constant average voltage can be applied via pulse width modulation (PWM), for example. In some implementations, such substantially constant average voltage is applied to the motor across all of the plurality of commutation steps of the motor over a single rotational cycle of the motor. In some implementations, such substantially constant average voltage is applied to the motor across all of the plurality of commutation steps of the motor over multiple rotational cycles of the motor, for example, two, five, ten, twenty, fifty, or any number of rotational cycles of the motor bounded by any of these values, among other values.

In some implementations, a method for controlling operation of a motor in a compressor includes: applying a substantially constant average voltage to the motor across all of a plurality of commutation steps of the motor during at least a first rotational cycle at step 301; determining actual motor speed for each of the commutation steps during such first rotational cycle at step 302; determining average motor speed over such first rotational cycle at step 304; determining a voltage pattern based on differences between the actual motor speeds for each commutation step during such first rotational cycle and the average motor speed during such first rotational cycle at step 306; and applying the voltage pattern during at least a second rotational cycle at step 308. Such voltage pattern can be determined as described above, for example, based at least on the differences between the actual motor speeds and the average motor speed during the first rotational cycle. The voltage pattern can be applied to the motor during the second rotational cycle also as described above, for example, by applying determined voltage values for each of the commutations steps during the second rotational cycle, which may vary from one another and/or vary from the substantially constant average voltage applied during the first rotational cycle. Such method can be iterative over additional rotational cycles of the motor. For example, the method can further include: determining actual motor speed for each of the commutation steps during such second rotational cycle; determining average motor speed over such second rotational cycle; determining a voltage pattern based at least on differences between the actual motor speeds for each commutation step during such second rotational cycle and the average motor speed during such second rotational cycle; and applying the voltage pattern during a third rotational cycle.

Variations of any of the methods discussed above possible. For example, in some variants: step 302 involves determining an average of the actual motor speeds for each commutation step for a previous number of cycles. For example, assuming three rotational cycles have occurred, step 302 can involve determining an average of the actual motor speeds for a particular commutation step during the first, second, and/or third rotational cycles. In such example, step 304 can involve determining an average of the averages determined in step 302 described immediately above. In such example, step 306 can involve determining a voltage pattern based on differences between the average of the actual motor speeds for each commutation step for the previous number of cycles and the average of the averages determined in step 304. While such example is described assuming three rotational cycles, such example can be utilized for any number of rotational cycles. Other variations are possible.

Motor speed oscillations may be greater or lesser depending on a flow setting selected for a portable oxygen concentrator (the flow setting being associated with a desired and/or predetermined average motor speed). In some implementations, step 306 and/or step 308 of method 300 is/are carried out only if one or more of the differences between the actual motor speeds and the average motor speed are above a threshold. For example, if the differences between the actual motor speeds at the motor commutation steps during a rotational cycle and the average motor speed over the rotational cycle are small, determination of the voltage pattern (step 306) and/or application of the voltage pattern for a subsequent rotational cycle (step 308) may be determined to be unnecessary. In some implementations, step 306 and/or 308 is/are only carried out if: at least one of the differences between the actual motor speeds at the motor commutation steps during a rotational cycle and the average motor speed over the rotational cycle is above a threshold; all of the differences between the actual motor speeds at the motor commutation steps during the rotational cycle and the average motor speed over the rotational cycle are above the threshold; and/or an average of the differences between the actual motor speeds at the motor commutation steps during the rotational cycle and the average motor speed over the rotational cycle are above the threshold.

Figure 4B:
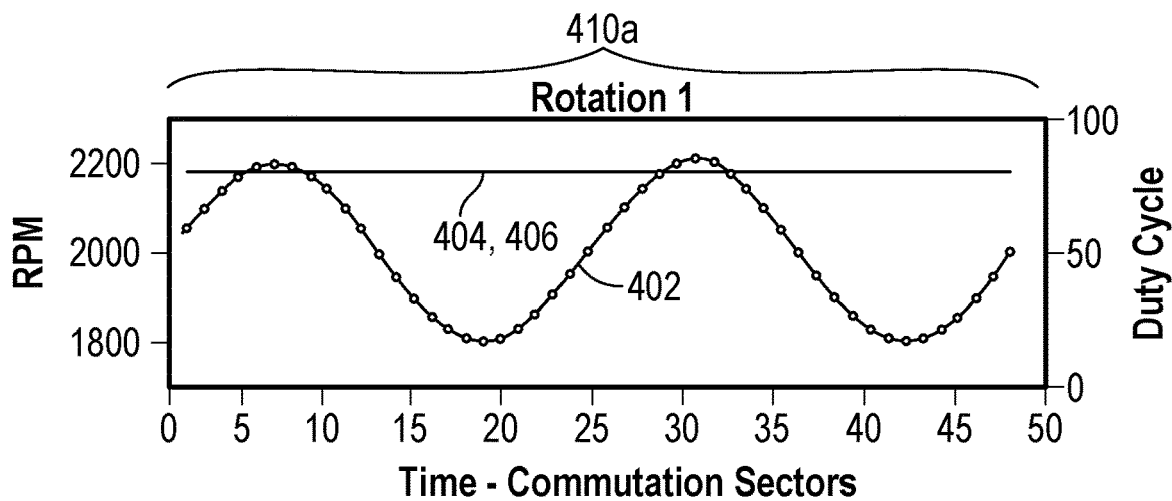
Figure 4C:
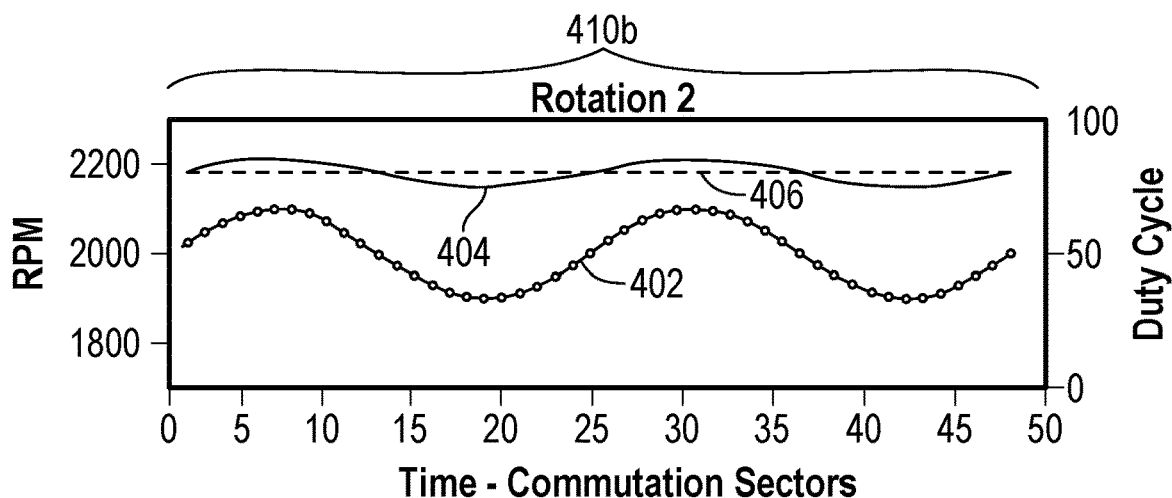
Figure 4D:
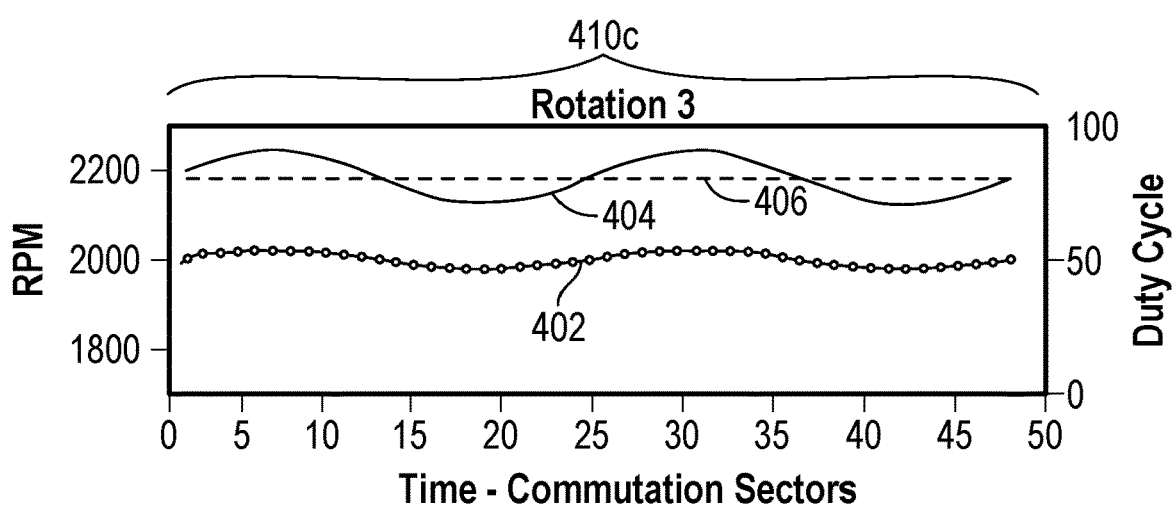

FIG. 4A visually illustrates an example method of controlling operation of a motor of a compressor in a portable oxygen concentrator. FIGS. 4B-4C illustrate enlarged views of portions of the graph shown in FIG. 4A. The graph shown in FIG. 4A shows actual motor speed (indicated with reference numeral 402) in revolutions per minute (RPM) over time and/or commutation sectors. Data points along line 402 can represent commutation points (for example, commutation magnetic states). FIG. 4A also shows duty cycle (indicated by reference numeral 404) and further illustrates a number of rotational cycles indicated by reference numerals 410a, 410b, 410c, 410d, and 410e. In cycle 410a, the duty cycle is kept constant, which can in turn provide a substantially constant average voltage to the motor. As shown, the actual motor speed over cycle 410a varies significantly, having a minimum value of about 1800 RPM and a maximum value of about 2200 RPM. These large speed oscillations can be caused from variable torque load imparted by piston(s) on the motor of a compressor as described previously. During cycles 410b-410e, duty cycle is varied, which in turn can of course cause variable voltage patterns to be applied to the motor that are different from the substantially constant average voltage applied during cycle 410a. The duty cycle pattern (and therefore voltage pattern) for each of cycles 410b-410e can be determined and applied as described above (for example, with respect to method 300). Actual motor speeds for each commutation step of the motor can be determined (for example, as described above with respect to step 302 of method 300) during cycle 410a and average motor speed during cycle 410a can be determined (for example, as described above with respect to step 304 of method 300). A voltage pattern can be determined (for example, as described above with respect to step 306), and can be applied to the motor during cycle 410b, for example, via application of an associated duty cycle pattern. Such process can be repeated for each of cycles 410c, 410d, and 410e in a similar manner. FIG. 4A illustrates how such process can be utilized to reduce the speed oscillations of the motor over time, as can be seen by the almost flat appearance of line 402 during cycle 410e. In some implementations of the motor control methods described herein (such as method 300), the voltage patterns for cycles 410b, 410c, 410d, 410e comprise a waveform shape that changes. For example, as can be seen in FIG. 4A, cycle 410c can have a waveform shape that differs from cycle 410b in that amplitudes (max/min points) are greater than amplitudes (max/min points) of a waveform shape for cycle 410b, and so on for successive ones of cycles 410d, and 410e. In some implementations, duty cycle of the motor is varied more: during cycle 410e than cycle 410d; during cycle 410d than cycle 410c; and/or during cycle 410c than cycle 410b.

As can be seen in FIG. 4A, the average RPM of the motor across cycles 410a-410e remains substantially constant at about 2000 RPM. As also can be seen in FIG. 4A, the average duty cycle (which can be associated with an average voltage) across cycles 410a-410e indicated by reference numeral 406 remains at about 80. Such average can be maintained when, for each of cycles 410b-410e, the "positive" area between the line 404 and line 406 is substantially equal to the "negative" area between the line 404 and line 406. Such average 406 can be associated with a particular flow setting, flow rate, and/or motor speed that is desired. Such average 406 may be changed when a user alters a flow setting of a portable oxygen concentrator, for example. As mentioned elsewhere herein, changing such average 406 can be referred to as "DC control" of the motor. Methods described herein vary the duty cycle/voltage over time (along the motor commutation steps) according to a determined voltage pattern which significantly minimizes the motor speed oscillations about such average, which in turn advantageously reduces noise and vibration of the motor. Varying the duty cycle/voltage over time and/or motor rotational cycles (for example, according to a voltage pattern) can be referred to as "AC control", and the utilization of information (for example, actual vs. average motor speed) for determining a voltage pattern may be referred to as a "feedforward scheme". Such control can vary the duty cycle/voltage over the motor commutation steps about such average 406, as illustrated by lines 404 and 406 in FIG. 4A.

Figure 4E:
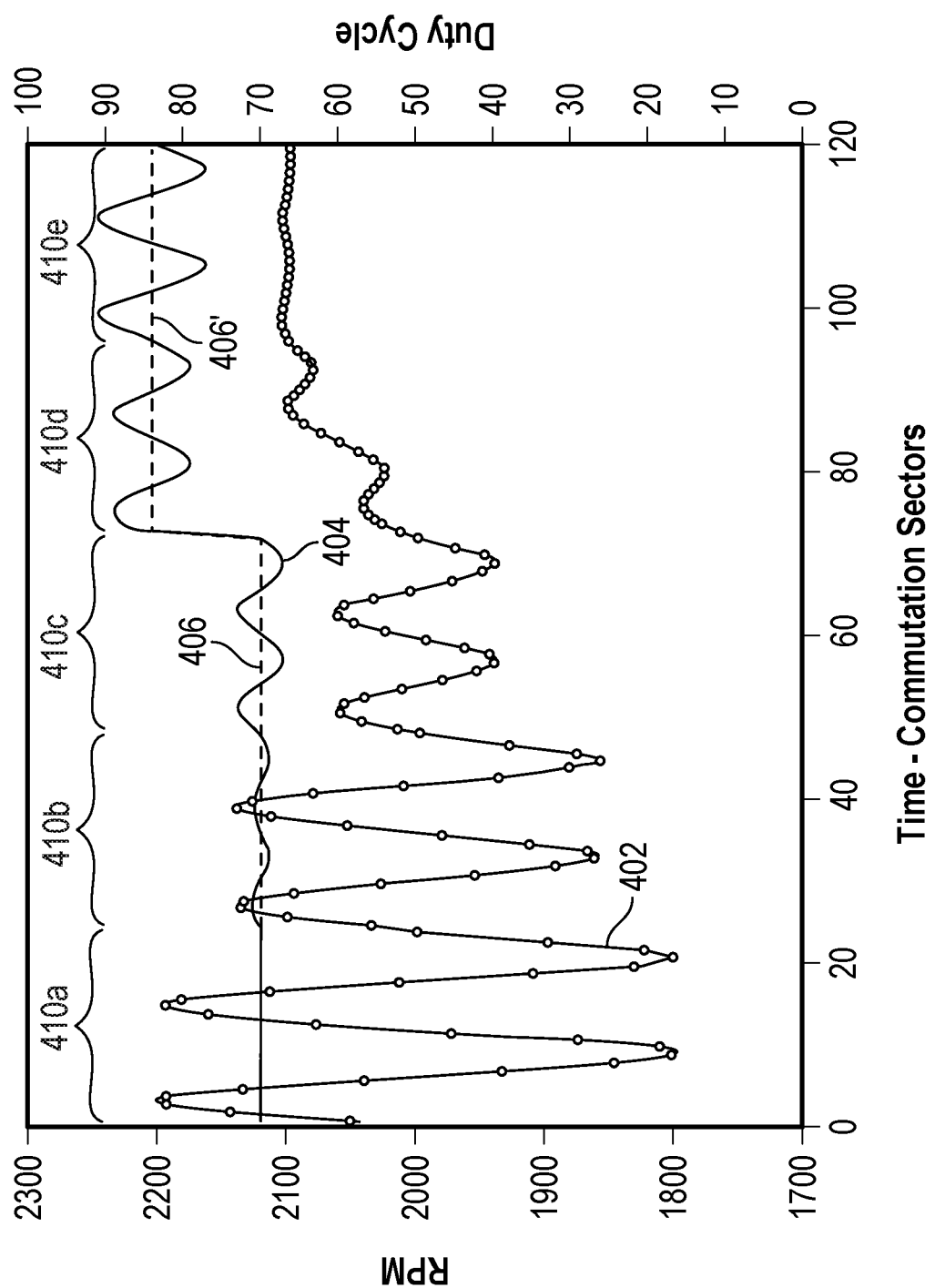

FIG. 4E illustrates a graph that is similar to FIG. 4A in many respects. However, FIG. 4E illustrates a change to the average duty cycle/voltage, which can be seen by comparing the average duty cycle/voltage 406 occurring during cycles 410a, 410b, and 410c (which is about 70), and an average duty cycle/voltage 406' occurring during cycles 410d and 410e (which is about 85). Such change may be associated with a change to a particular flow setting, flow rate, and/or motor speed of the portable oxygen concentrator. For example, such change may represent a change from a first flow setting having a first flow rate to a second flow setting having a second flow rate that is lager than the first flow rate. As mentioned previously, controlling the average duty cycle/voltage (e.g., from line 406 to line 406') may be referred to as "DC control" of the motor, and such control can be achieved by a conventional PD or PID controller where average motor speed is used as a feedback input, for example. Such control is in contrast to varying the duty cycle/voltage of the motor during rotational cycle(s) in accordance with method 300 for example, which may be referred to as "AC control" as also mentioned previously. The "jump" from line 406 to line 406' in FIG. 4E may alternatively or additionally represent changes that may occur during a PSA cycle of the portable oxygen concentrator which houses the compressor and motor. Regardless of whether average duty cycle/voltage is modified during one or more rotational cycles, the method described herein can still be utilized to vary the duty cycle/voltage over time (along the motor commutation steps) according to a determined voltage pattern to reduce speed oscillations of the motor. For example, despite the average motor speed over cycles 410a-410c being different (lower) than the average motor speed over cycles 410d, 410e (see line 402 in FIG. 4E), the methods described herein can cause the motor speed to settle around the new average to reduce speed oscillations and in turn, noise and vibration of the motor. Any of the motor control methods discussed herein can include changing average duty cycle/voltage of a motor alone or in combination with any motor control steps (such as those described with respect to method 300).

Although FIGS. 4A-4E only show example cycles 410a-410e of a motor, the number of cycles is utilized for ease of illustration and description, and is not intended to be limiting. It is to be understood that the method described herein may be utilized over a significantly larger number of cycles, which may be occurring over a very short time frame (e.g., seconds or milliseconds) depending on operation of the motor. It is also to be understood that the duty cycle/voltage patterns associated with one of cycles 410a-410e discussed above may occur over more than one rotational cycle of the motor. For example, multiple of any of cycles 410a-410e may occur during motor operation when any of the methods discussed herein are employed. Each of cycles 410a-410e, for example, as illustrated in FIGS. 4A and 4E, may represent more than one (for example, two) motor rotational cycles.

Figure 5A:
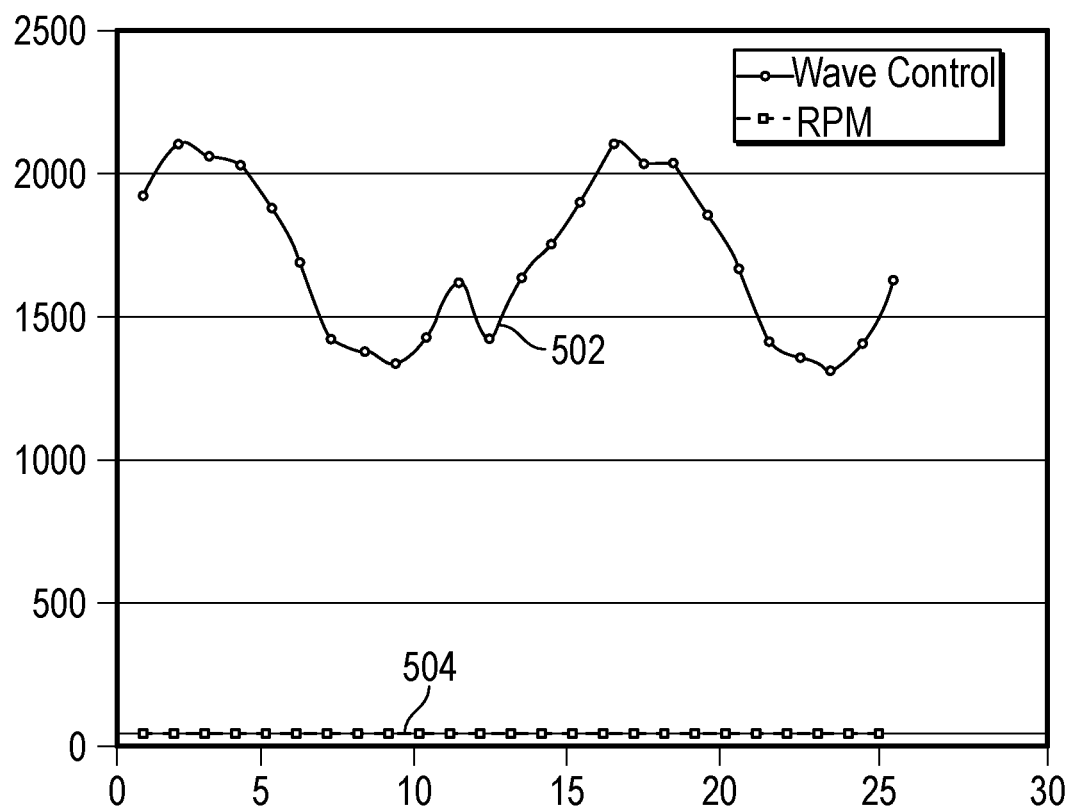
FIGS. 5A-6 graphically illustrate experimental data associated with motor control methods in accordance with aspects of this disclosure.
Figure 5B:
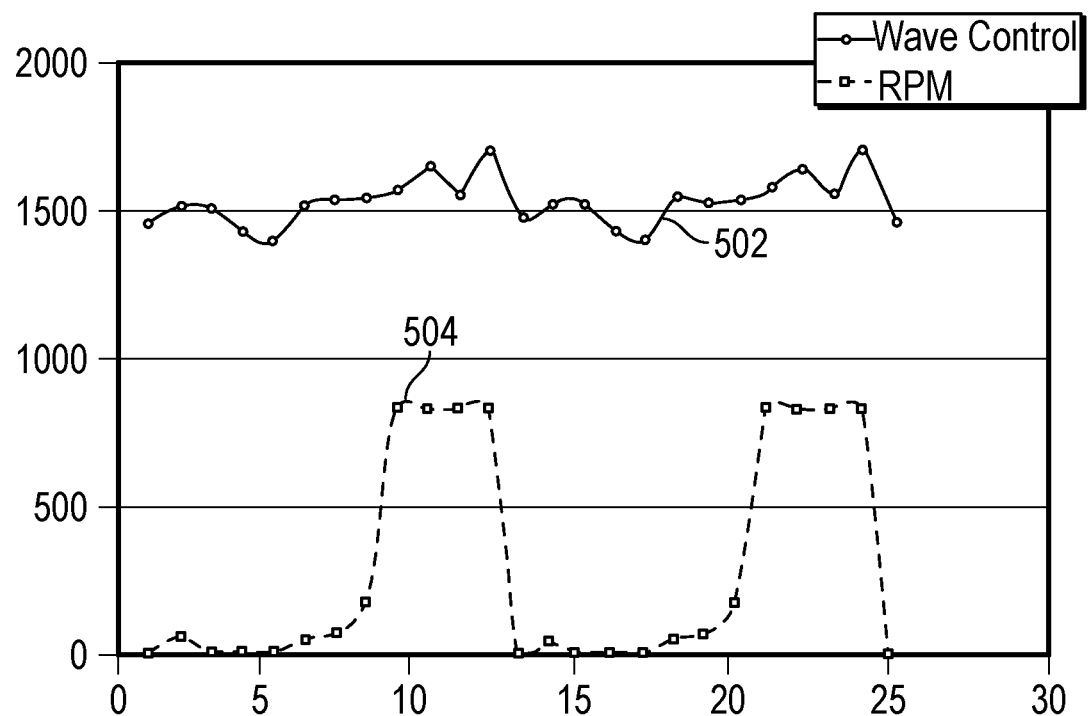

FIG. 5A illustrates empirical data of actual motor speed values (line 502, given name "RPM") where motor control methods described herein are not utilized (e.g., a variable voltage pattern is not determined and applied, which is visually represented by the flat line 504 given the name "Wave Control"). FIG. 5B illustrates empirical data of actual motor speed values (line 502) where methods described herein are utilized (line 504). As can be seen by comparing FIGS. 5A and 5B, the actual motor speed oscillations are significantly less when utilizing motor control methods described herein.

With reference to FIGS. 4A-5B, the voltage patterns described herein can comprise a plurality of values (for example, associated with the plurality of commutations steps of the motor) that can have a waveform shape. Such waveform can be oscillating, as shown, and as discussed elsewhere herein.

Figure 6:
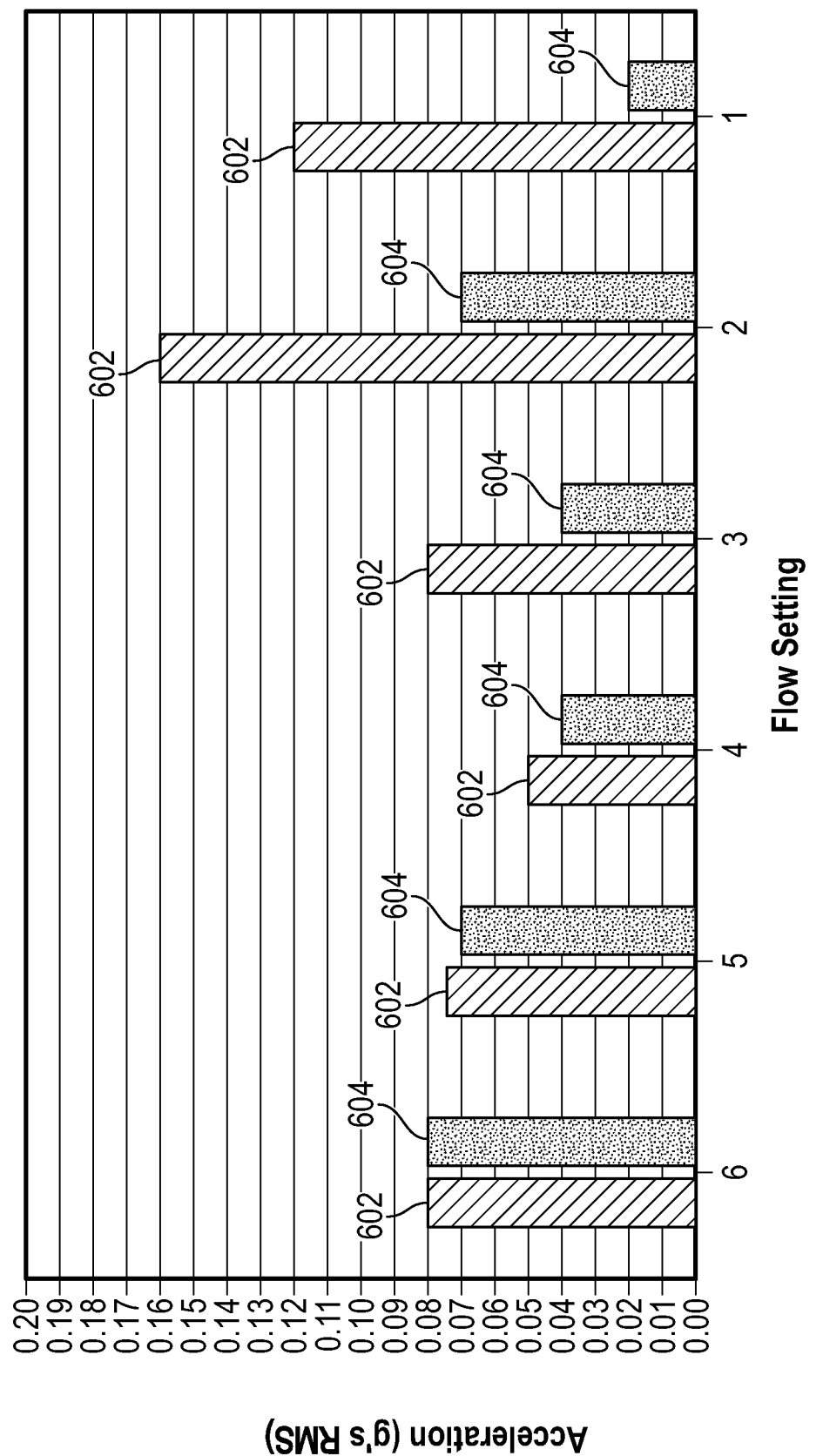

FIG. 6 illustrates vibration data experienced in an example portable oxygen concentrator at differing flow settings (flow settings "1" through "6"). In this example, flow setting "6" is associated with a motor speed between 3400 and 3500 RPM, flow setting "5" is associated with a motor speed between 2800 and 2900 RPM, flow setting "4" is associated with a motor speed between 2300 and 2400 RPM, flow setting "3" is associated with a motor speed between 1800 and 1900 RPM, flow setting "2" is associated with a motor speed between 1300 and 1400 RPM, and flow setting "1" is associated with a motor speed between 1050 and 1150 RPM. Box 602 represents acceleration values when motor control methods such as any of those described herein are not employed and box 604 represents acceleration values when motor control methods such as any of those described herein are employed. As shown, in some compressors (and some portable oxygen concentrators having such compressors), the motor control methods described herein have a significant effect on reducing vibration, especially at lower flow settings where motor RPMs are below 2000.

Although the methods described herein can dramatically improve speed oscillations in a motor of a portable oxygen concentrator, such techniques may, in some cases, impact life of a battery of the portable oxygen concentrator. Despite the net work across a cycle being the same, the increased variation in the peak currents resulting from utilization of motor control methods described herein may produce a small power penalty in some cases. For this as well as other considerations, it can be useful to have the capability to situationally control, either by user and/or automatically, when motor control methods are utilized. In some implementations, a controller of the portable oxygen concentrator (such as any of those discussed herein) is configured to apply motor control methods (such as any of those described herein) only when a charge level of the battery is above a threshold. For example, in some implementations, the controller does not carry out step 302, step 304, step 306, and/or step 308 (each of which are described above) unless the charge level of the battery is above the threshold. In some implementations, responsive to the controller determining that the battery is at or above the threshold, the controller initiates any or all of step 302, step 304, step 306, and/or step 308. Such threshold may be 5%, 10%, 15%, 20%, 25%, 30%, 35%, 40%, or 50% charge level of the battery, for example.

Any of the controllers described herein can be configured to enable, disable, and/or tune any of the motor control methods described herein to vary a degree of motor control applied based on target motor speed (e.g., RPM) and/or acceleration measured by and/or within a portable oxygen concentrator. For example, in some implementations, the controller does not carry out step 302, step 304, step 306, and/or step 308 (each of which are described above) unless the average RPM of the motor (see, e.g., line 406 in FIGS. 4A-4D) is within a predetermined range (e.g., less than about 2000 RPM, less than about 1900 RPM, less than about 1800 RPM, less than about 1700 RPM, less than about 1600 RPM, less than about 1500 RPM, less than about 1400 RPM, less than about 1300 RPM, or less than about 1200 RPM). Such predetermined range may be associated with higher motor speed oscillation levels, for example. As another example, in some implementations, the controller is configured to apply motor control methods (such as any of those described herein) only when measured acceleration (for example, measured using an accelerometer of a portable oxygen concentrator) is above a threshold (for example, 0.02 g, 0.05 g, 0.10 g, or 0.15 g). In some implementations, responsive to the controller determining that acceleration levels (for example, of the portable oxygen concentrator and/or a compressor thereof) are at or above the threshold, the controller initiates any or all of step 302, step 304, step 306, and/or step 308 (each of which are described above).

Figure 7A:
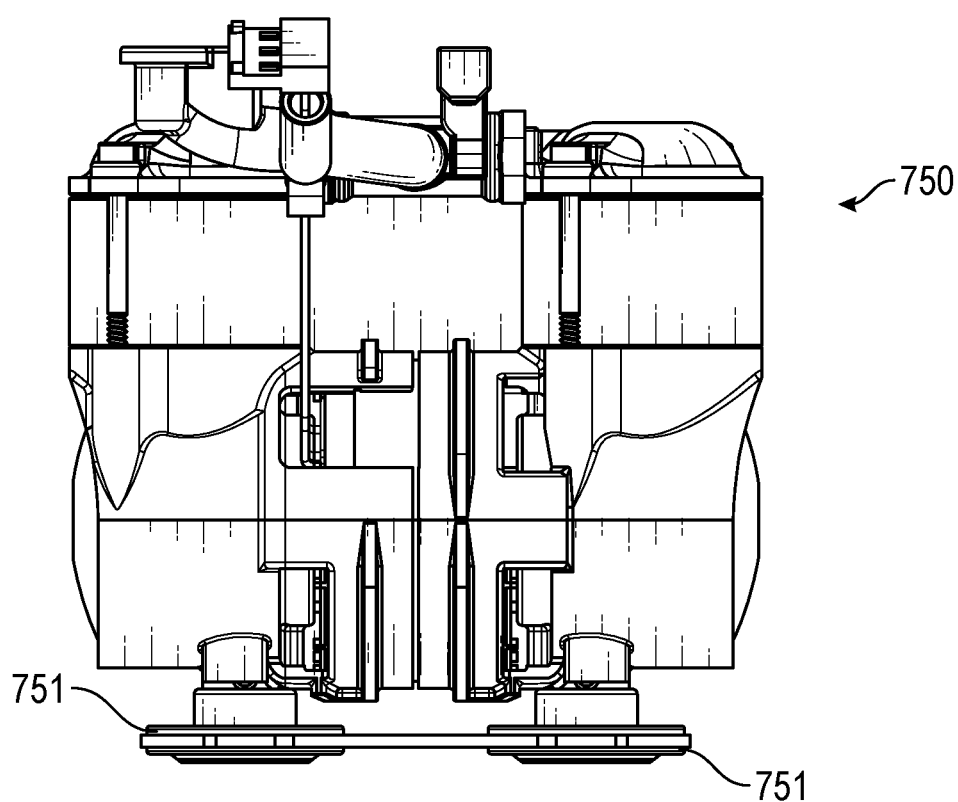
Figure 7B:
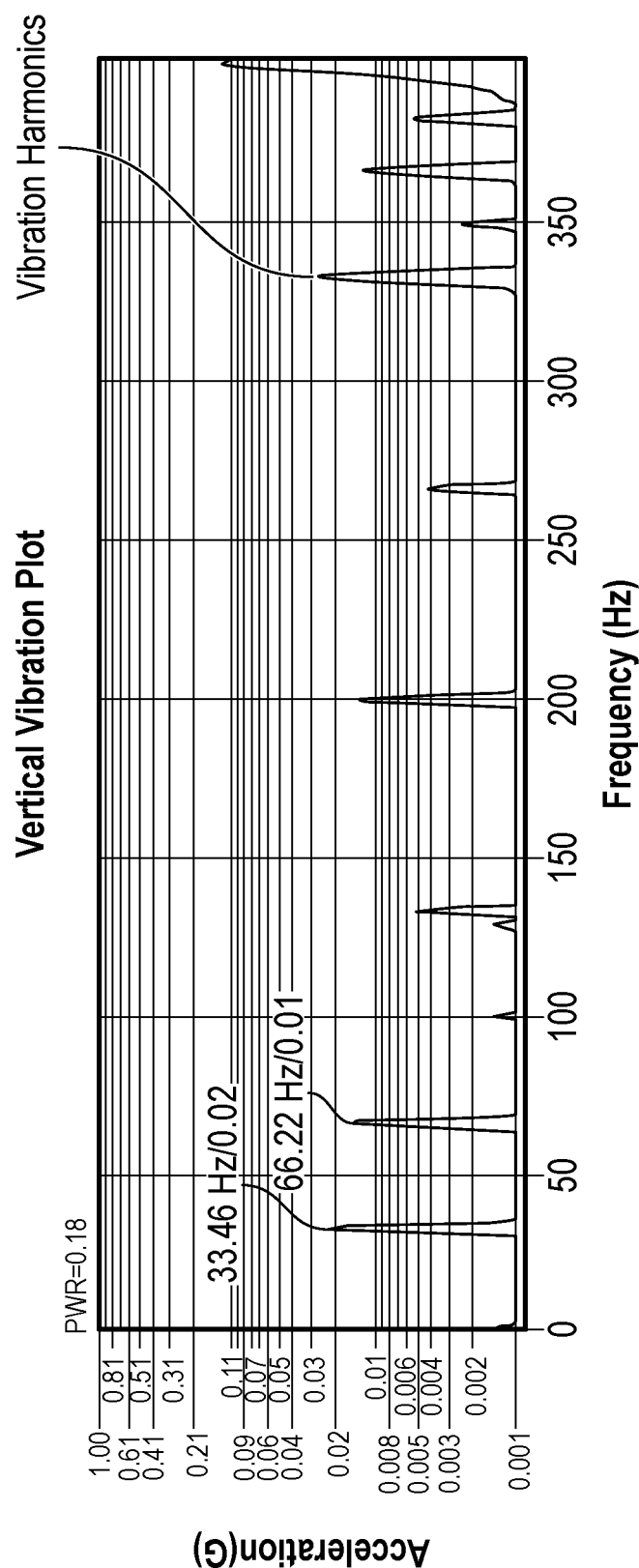
FIGS. 7B-7C illustrate vibration plots and harmonics in accordance with aspects of this disclosure.
Figure 7C:
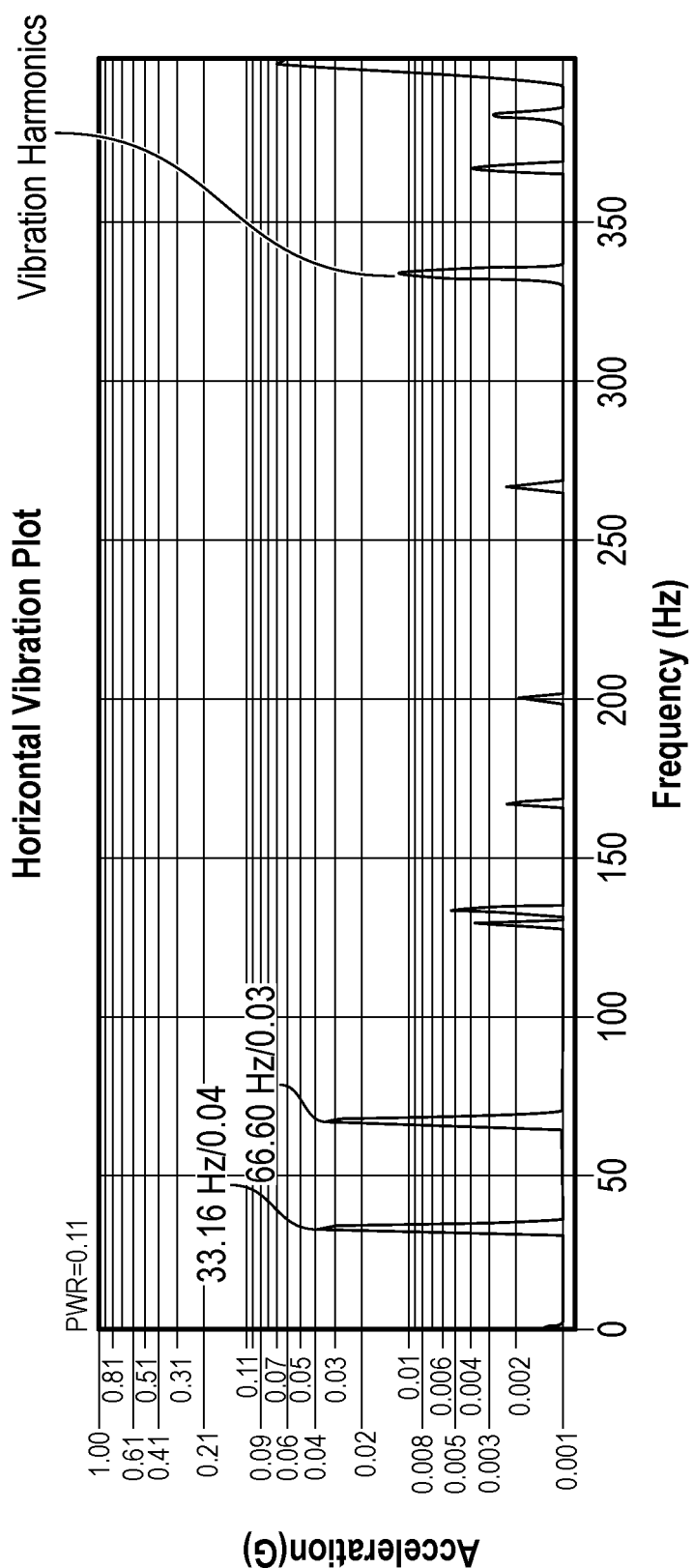

Any of the controllers described herein can be configured to enable, disable, and/or tune any of the motor control methods described herein to vary a degree of motor control applied based on one or more harmonic frequencies associated with one or more components within the portable oxygen concentrator (for example, based on whether the motor speed is within a threshold range associated with compressor mount harmonic frequencies that can cause particularly poor vibration isolation). FIG. 7A illustrates a compressor 750 (which may be similar or identical to any of the compressors discussed herein) and compressor mounts 751 (which may be referred to herein as "vibration mounts") which can connect and/or be positioned between the compressor 750 and another portion of a portable oxygen concentrator that houses the compressor 750. Compressor mounts 751 can be made of a compliant material that for most compressor speeds can be designed to provide adequate sound and vibration damping. As with the limitations inherent in the use of counter weights, the compressor mounts 751 may be constrained in size and weight and may not provide full vibration isolation across all operating motor speed ranges of the portable oxygen concentrator while still being stiff enough to prevent the compressor 750 from use damage, such as from hitting the internals of the portable oxygen concentrator when dropped or used during ambulation. If the compressor mounts 751 are so soft that they isolate all vibration resulting in the compressor 750 striking the internals of the portable oxygen concentrator, that strike may add unacceptable levels of sound and vibration or damage other components of the portable oxygen concentrator. Designing the compressor mounts 751 within these system constraints can result in vibration harmonic frequencies that can transmit undesirable amounts of vibration to the portable oxygen concentrator when the motor operates at or near speeds associated with those harmonic peaks. These frequencies largely are directly related to motor speed. FIGS. 7B-7C illustrate example vibration harmonics. In some implementations, the controller determines whether to carry out motor control methods (such as any of those discussed herein) based on a comparison of an average motor RPM and a predetermined RPM range associated with one or more harmonic frequencies of the compressor mounts 751. For example, in some implementations, the controller carries out step 302, step 304, step 306, and/or step 308 (each of which are described above) if the average RPM of the motor (see, e.g., line 406 in FIGS. 4A-4D) is within a predetermined range associated with one or more harmonic frequencies of the compressor mounts 751 (for example, between about 1200 RPM and 2000 RPM or between about 1400 RPM and 1600 RPM). In some implementations, the controller carries out step 302, step 304, step 306, and/or step 308 (each of which are described above) if the average RPM of the motor (see, e.g., line 406 in FIGS. 4A-4D) is outside of such predetermined range. As described above, the average RPM of the motor may be associated with one of a plurality of flow settings of the portable oxygen concentrator. Accordingly, in some implementations, the controller carries out step 302, step 304, step 306, and/or step 308 (each of which are described above) only for certain ones of the plurality of flow setting of the portable oxygen concentrator. In some implementations, employing motor control methods may allow smoothing out of vibration.

Although various methods and systems for controlling operation of a motor have been described herein with respect to implementations of portable oxygen concentrators, the disclosed methods and systems are not so limited. Rather, any of the motor control methods and systems described herein can be utilized with motors in a variety of systems and devices other than portable oxygen concentrators.

Additional Considerations and Terminology

The embodiments described herein are examples. Modifications, rearrangements, substitute processes, alternative elements, etc. may be made to these embodiments and still be encompassed within the teachings set forth herein. One or more of the processes described herein may be carried out by one or more processing and/or digital devices, suitably programmed.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

The various illustrative processing, data display, and user interfaces described in connection with the embodiments disclosed herein can be implemented as electronic hardware, computer software, or combinations of both. To clearly illustrate this interchangeability of hardware and software, various illustrative components, blocks, and modules have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, for example. A processor can also be implemented as a combination of computing devices, e.g., a combination of a DSP and a microprocessor, a plurality of microprocessors, one or more microprocessors in conjunction with a DSP core, or any other such configuration.

The elements of the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An example storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally" and "substantially" may refer to an amount that is within less than or equal to 10% of, within less than or equal to 5% of, or within less than or equal to 1% of the stated value, amount, or characteristic.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A portable oxygen concentrator comprising:
a housing;
an inlet configured to allow ambient air to flow into an interior of the housing;
a gas separation system positioned within the interior;
a compressor positioned within the interior and arranged between the inlet and the gas separation system, the compressor configured to receive and pressurize at least a portion of the ambient air flowing into the interior and direct the portion of the ambient air toward the gas separation system, the gas separation system comprising one or more adsorbent beds configured to separate oxygen from one or more other elements in the portion of the ambient air, the compressor comprising:
a motor;
at least one chamber for receiving the portion of the ambient air; and
at least one piston coupled to the motor and configured to be moved within the at least one chamber via rotation of the motor; and
a controller configured to:
cause a substantially constant average voltage to be applied to the motor during a first rotational cycle of the motor, said motor applying a motor torque to the at least one piston responsive to the application of the substantially constant average voltage, said at least one piston applying a variable torque load to the motor that opposes the motor torque and varies as the at least one piston moves within the at least one chamber;
determine, for each of a plurality of commutation steps of the motor during the first rotational cycle, an actual motor speed;
determine an average motor speed during the first rotational cycle;
determine a plurality of correction terms, each of the plurality of correction terms comprising a difference between the actual motor speed for one of the plurality of commutation steps of the motor during the first rotational cycle and the average motor speed during the first rotational cycle;
determine a voltage pattern comprising a plurality of voltage values, each of the plurality of voltage values determined based at least on one of the plurality of correction terms, wherein at least some of the plurality of voltage values differ from the substantially constant average voltage; and
cause each of the plurality of voltage values of the voltage pattern to be applied to the motor during a respective one of the plurality of commutation steps for at least a second rotational cycle of the motor, said application of the voltage pattern reducing differences between the applied motor torque and the variable torque load, thereby minimizing speed oscillations of the motor and noise and vibration of the compressor within the portable oxygen concentrator.

2. The portable oxygen concentrator of claim 1, wherein the at least one chamber comprises two chambers and the at least one piston comprises two pistons configured in a reciprocating arrangement.

3. The portable oxygen concentrator of claim 1, wherein an average of the plurality of voltage values of the voltage pattern applied to the motor during the second rotational cycle is substantially equal to the substantially constant average voltage applied to the motor during the first rotational cycle.

4. A portable oxygen concentrator comprising:
a compressor configured to pressurize and direct ambient air flowing into an interior of the portable oxygen concentrator towards a gas separation system of the portable oxygen concentrator, said compressor comprising a motor, at least one chamber for receiving at least a portion of the ambient air, and at least one piston operably coupled to the motor and configured to be moved within the at least one chamber via rotation of the motor, said motor applying a motor torque to the at least one piston responsive to rotation of the motor, said at least one piston applying a variable torque load to the motor that opposes said motor torque and varies as the at least one piston moves within the at least one chamber; and
a controller configured to:
determine an actual motor speed for each of a plurality of commutation steps of the motor during a first rotational cycle of the motor;

determine an average motor speed during the first rotational cycle, wherein the average motor speed during the first rotational cycle differs from at least one of the actual motor speeds for the plurality of commutation steps during the first rotational cycle; and determine a voltage pattern to be used during a second rotational cycle of the motor, said voltage pattern comprising a plurality of voltage values determined based at least on a comparison of the average motor speed during the first rotational cycle and the actual motor speeds for the plurality of commutation steps of the motor during the first rotational cycle, said voltage pattern usable to reduce differences between said applied motor torque and said variable torque load, thereby minimizing speed oscillations of the motor and noise and vibration of the compressor, wherein at least one of said plurality of voltage values differs from at least one other one of said plurality of voltage values.

5. The portable oxygen concentrator of claim 4, wherein the controller is further configured to cause a substantially constant average voltage to be applied to the motor during the first rotational cycle of the motor, said motor applying said motor torque to the at least one piston responsive to said application of the substantially constant average voltage.

6. The portable oxygen concentrator of claim 5, wherein:
each of the plurality of voltage values associated with a respective one of the plurality of commutation steps during the second rotational cycle is greater than said substantially constant average voltage when an associated one of the actual motor speeds during the respective one of the plurality of commutation steps of the first rotational cycle is less than said average motor speed during the first rotational cycle; and
each of the plurality of voltage values associated with the respective one of the plurality of commutation steps during the second rotational cycle is less than said substantially constant average voltage when the associated one of the actual motor speeds during the respective one of the plurality of commutation steps of the first rotational cycle is greater than said average motor speed during the first rotational cycle.

7. The portable oxygen concentrator of claim 4, wherein the controller is further configured to cause said voltage pattern to be applied to the motor during the second rotational cycle of the motor.

8. The portable oxygen concentrator of claim 4, further comprising a battery, wherein the controller is further configured to cause said voltage pattern to be applied to the motor during the second rotational cycle of the motor only if a charge level of said battery is above a threshold.

9. The portable oxygen concentrator of claim 4, wherein:
said voltage pattern is a first voltage pattern; and
the controller is further configured to:
determine an actual motor speed for each of said plurality of commutation steps of the motor during the second rotational cycle of the motor;
determine an average motor speed during the second rotational cycle of the motor; and
determine a second voltage pattern to be used during a third rotational cycle of the motor, said second voltage pattern comprising a plurality of voltage values determined based at least on a comparison of the average motor speed during the second rotational cycle and the actual motor speeds for the plurality of commutation steps of the motor during the second rotational cycle, wherein at least one of said plurality of voltage values of said second voltage pattern differs from at least one other one of said plurality of voltage values of said second voltage pattern.

10. The portable oxygen concentrator of claim 9, wherein at least one of said plurality of voltage values of the second voltage pattern differs from at least one of said plurality of voltage values of the first voltage pattern.

11. The portable oxygen concentrator of claim 9, wherein the average motor speed during the second rotational cycle of the motor is substantially equal to the average motor speed during the first rotational cycle of the motor.

12. The portable oxygen concentrator of claim 9, wherein the average motor speed during the second rotational cycle of the motor differs from at least one of the actual motor speeds for the plurality of commutation steps during the second rotational cycle.

13. The portable oxygen concentrator of claim 9, wherein the controller is further configured to:
determine a plurality of average actual motor speeds, each of said plurality of average actual motor speeds comprising an average of the actual motor speeds during at least the first and second rotational cycles for one of the plurality of commutation steps;
determine an average of said plurality of average actual motor speeds; and
determine a third voltage pattern to be used during a fourth rotational cycle of the motor, said third voltage pattern comprising a plurality of voltage values determined based at least on a comparison of:
said average of said plurality of average actual motor speeds; and
said plurality of average actual motor speeds.

14. The portable oxygen concentrator of claim 13, wherein said third voltage pattern is different than at least one of said first and second voltage patterns.

15. A method of controlling operation of a motor of a compressor in a portable oxygen concentrator to reduce noise and vibration during use, said compressor configured to pressurize and direct ambient air flowing into an interior of the portable oxygen concentrator towards a gas separation system of the portable oxygen concentrator, said compressor comprising said motor, at least one chamber for receiving at least a portion of said ambient air, and at least one piston operably coupled to said motor and configured to be moved within the at least one chamber via rotation of said motor, said motor applying a motor torque to the at least one piston responsive to rotation of said motor, said at least one piston applying a variable torque load to the motor that opposes said motor torque and varies as the at least one piston moves within the at least one chamber, wherein the method comprises:
determining an actual motor speed for each of a plurality of commutation steps of the motor during a first rotational cycle;
determining an average motor speed during the first rotational cycle, wherein the average motor speed during the first rotational cycle differs from at least one of the actual motor speeds for the plurality of commutation steps during the first rotational cycle; and
determining a voltage pattern to be used during a second rotational cycle of the motor, said voltage pattern comprising a plurality of voltage values determined based at least on a comparison of the average motor speed during the first rotational cycle and the actual motor speeds for the plurality of commutation steps of the motor during the first rotational cycle, said voltage pattern usable to reduce differences between said applied motor torque and said variable torque load, thereby minimizing speed oscillations of the motor and noise and vibration of the compressor, wherein at least one of said plurality of voltage values differs from at least one other one of said plurality of voltage values.

16. The method of claim 15, further comprising applying a substantially constant average voltage to the motor during the first rotational cycle of the motor, said motor applying said motor torque to the at least one piston responsive to said application of the substantially constant average voltage.

17. The method of claim 16, wherein at least one of said plurality of voltage values differs from said substantially constant average voltage.

18. The method of claim 16, wherein:
each of the plurality of voltage values associated with a respective one of the plurality of commutation steps during the second rotational cycle is greater than said substantially constant average voltage when an associated one of the actual motor speeds during the respective one of the plurality of commutation steps of the first rotational cycle is less than said average motor speed during the first rotational cycle; and
each of the plurality of voltage values associated with the respective one of the plurality of commutation steps during the second rotational cycle is less than said substantially constant average voltage when the associated one of the actual motor speeds during the respective one of the plurality of commutation steps of the first rotational cycle is greater than said average motor speed during the first rotational cycle.

19. The method of claim 15, wherein said voltage pattern is a first voltage pattern and wherein the method further comprises:
determining an actual motor speed for each of said plurality of commutation steps of the motor during the second rotational cycle of the motor;
determining an average motor speed during the second rotational cycle of the motor; and
determining a second voltage pattern to be used during a third rotational cycle of the motor, said second voltage pattern comprising a plurality of voltage values determined based at least on a comparison of the average motor speed during the second rotational cycle and the actual motor speeds for the plurality of commutation steps of the motor during the second rotational cycle, wherein at least one of said plurality of voltage values of said second voltage pattern differs from at least one other one of said plurality of voltage values of said second voltage pattern.

20. The method of claim 19, wherein at least one of said plurality of voltage values of the second voltage pattern differs from at least one of said plurality of voltage values of the first voltage pattern.

* * * * *